United States Patent [19]
Yamatsu et al.

[11] Patent Number: 4,742,058
[45] Date of Patent: May 3, 1988

[54] POLYPRENYL COMPOUND, PROCESS FOR THE PRODUCTION THEREOF AND DRUG CONTAINING THE SAME

[75] Inventors: Isao Yamatsu, Ushiku; Takeshi Suzuki, Ushikumachi; Shinya Abe, Kukizakimachi; Kouji Nakamoto, Tsuchiura; Akiharu Kajiwara, Yatabemachi; Tohru Fujimori, Toyosatomachi; Koukichi Harada, Yatabe; Shinichi Kitamura, Tokyo, all of Japan

[73] Assignee: Eisai Co., Ltd., Tokyo, Japan

[21] Appl. No.: 885,321

[22] Filed: Jul. 14, 1986

Related U.S. Application Data

[63] Continuation of Ser. No. 554,423, Nov. 23, 1983, abandoned.

[30] Foreign Application Priority Data

Nov. 30, 1982 [JP] Japan ................... 57-208678

[51] Int. Cl.⁴ ................... A61K 31/535; C07D 295/18

[52] U.S. Cl. .................. 514/237.8; 514/319; 514/326; 514/330; 514/354; 514/617; 514/238.8; 544/164; 544/168; 546/244; 546/247; 546/309; 564/157; 564/180; 564/183; 564/208; 564/215; 564/224; 564/342; 564/345

[58] Field of Search ............... 544/164, 168; 546/244, 546/247, 309; 564/208, 215, 224, 157, 183, 180, 342, 345; 514/234, 319, 326, 330, 354, 617

[56] References Cited

U.S. PATENT DOCUMENTS

| | | | |
|---|---|---|---|
| 2,595,907 | 5/1952 | Thomas | 564/204 |
| 2,649,438 | 8/1953 | Bruson | 564/208 |
| 2,760,977 | 8/1956 | Feuer | 564/208 |
| 3,822,276 | 7/1974 | Meisels | 546/309 |
| 4,021,224 | 5/1977 | Pallos | 564/204 |
| 4,148,926 | 4/1979 | Baker | 564/215 |
| 4,338,251 | 7/1982 | Sato et al. | |
| 4,346,109 | 8/1982 | Yamatsu et al. | |
| 4,456,603 | 6/1984 | Yamatsu | 546/226 |

Primary Examiner—C. Warren Ivy
Assistant Examiner—Alex H. Walker
Attorney, Agent, or Firm—Flynn, Theil, Boutell & Tanis

[57] ABSTRACT

A novel polyprenyl compound such as a polyprenyl carboxylic acid amide is disclosed. It has antithrombic and antiplatelet aggregation activity.

35 Claims, No Drawings

POLYPRENYL COMPOUND, PROCESS FOR THE PRODUCTION THEREOF AND DRUG CONTAINING THE SAME

This application is a continuation of application Ser. No. 554,423, filed Nov. 23, 1983 and now abandoned.

This invention relates to a polyprenyl compound having excellent medicinal activity. More particularly, the invention relates to a polyprenyl compound of the formula (I):

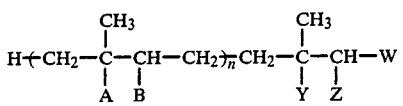

wherein A, B, Y and Z are each hydrogen, or the pair (1) A and B and/or the pair (2) Y and Z together represent a direct valence bond between the carbon atoms to which they are attached, thereby forming a double bond therebetween; W is a group of —COR or a group of X; and n is zero or an integer of 1 to 4 when W is the group of —COR; n is an integer of 1 to 3 when W is the group of X.

R in the formula is selected from:

(1) a group of the formula

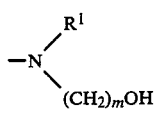

wherein $R^1$ is hydrogen or lower alkyl and m is an integer of from 1 to 5;

(2) a group of the formula

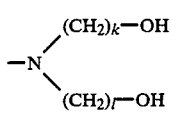

wherein k and l are the same or different and each is an integer of from 1 to 5;

(3) a group of the formula

—NHCH$_2$COOR$^2$ wherein $R^2$ is hydrogen, lower alkyl or aryl, preferably alkyl or aryl;

(4) a group of the formula

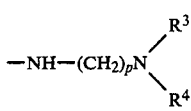

wherein p is an integer of from 0 to 5 and $R^3$ and $R^4$ are each hydrogen or lower alkyl, preferably lower alkyl;

(5) a group of the formula

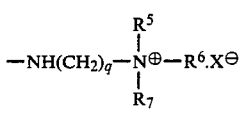

wherein q is an integer of from 1 to 5, $R^5$, $R^6$ and $R^7$ are each hydrogen or lower alkyl, preferably lower alkyl, and X is a halogen;

(6) a group of the formula

wherein r is 2 or 3 and $R^8$ is lower alkyl;

(7) a group of the formula

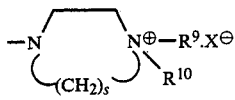

wherein s is 2 or 3, $R^9$ and $R^{10}$ are each lower alkyl and X is a halogen;

(8) a group of the formula

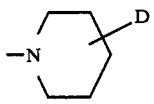

wherein D is a group of the formula —(CH$_2$)$_t$OH, in which t is an integer of from 0 to 5, a group of the formula

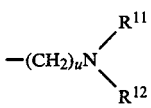

wherein u is an integer of from 0 to 5 and $R^{11}$ and $R^{12}$ are each hydrogen or lower alkyl, or a group of the formula

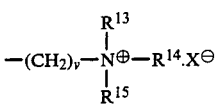

wherein v is an integer of from 0 to 5, $R^{13}$, $R^{14}$ and $R^{15}$ are each lower alkyl and X is a halogen;

(9) a group of the formula

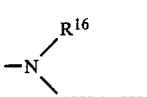

wherein $R^{16}$ is hydrogen or lower alkyl and w is an integer of from 1 to 5;

(10) a group of the formula

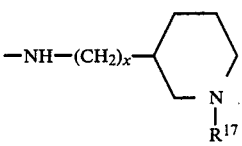

wherein R$^{17}$ is hydrogen or lower alkyl and x is an integer of from 0 to 5, preferably from 1 to 5; and
(11) a group of the formula

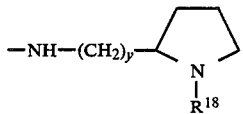

wherein R$^{18}$ is hydrogen or lower alkyl and y is an integer of 1 to 5, X is selected from
(1) a group of the formula

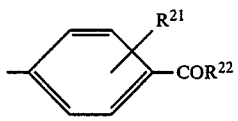

wherein R$^{22}$ is a group of the formula

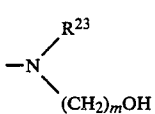

wherein R$^{23}$ is hydrogen or lower alkyl R$^{21}$ is hydrogen, lower alkyl or halogen and m is an integer of from 1 to 5;
a group of the formula

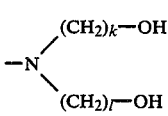

wherein k and l are the same or different and each is an integer of from 1 to 5;
a group of the formula

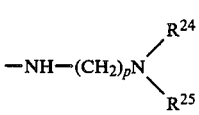

wherein p is an integer of from 0 to 5 and R$^{24}$ and R$^{25}$ are each hydrogen or lower alkyl; and a group of the formula

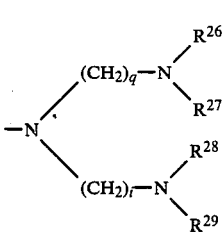

wherein q and i are each an integer of 1 to 5 and R$^{26}$, R$^{27}$, R$^{28}$ and R$^{29}$ are each a lower alkyl, and R$^{21}$ is hydrogen, a lower alkyl or a halogen atom,
(2) a group of the formula

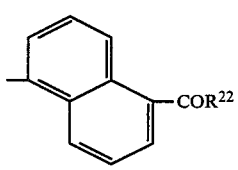

wherein K and L are both hydrogen or represent a direct valence bond the carbon atom to which they are attached,
(3) a group of the formula

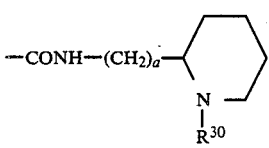

(4) a group of the formula

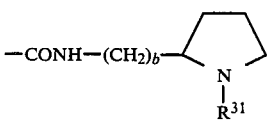

(5) a group of the formula

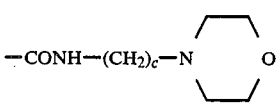

(6) a group of the formula

—CONH—(CH$_2$)$_a$—[piperidine with R$^{30}$ on N]

wherein a is zero or an integer of 1 to 5, and R$^{30}$ is a lower alkyl,
(7) a group of the formula —CONH—(CH$_2$)$_b$—[pyrrolidine with R$^{31}$ on N]

wherein b is zero or an integer of 1 to 5 and R$^{31}$ is a lower alkyl,
(8) a group of the formula —CONH—(CH$_2$)$_c$—N[morpholine]O wherein c is zero or an integer of 1 to 5,
(9) a group of the formula

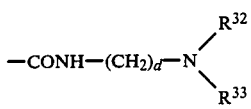

wherein d is zero or an integer of 1 to 5 and $R^{32}$ and $R^{33}$ are each a lower alkyl,
(10) a group of the formula

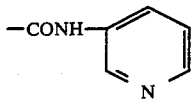

(11) a group of the formula

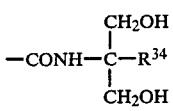

wherein $R^{34}$ is a lower alkyl,
(12) a group of the formula

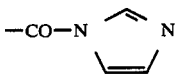

(13) a group of the formula —CONH—CH$_2$CH(OH)CH$_2$OH
(14) a group of the formula

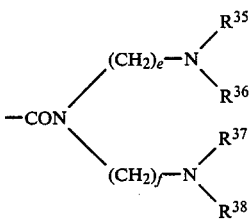

wherein e and f are each an integer of 1 to 5 and $R^{35}$, $R^{36}$, $R^{37}$ and $R^{38}$ are each hydrogen or a lower alkyl,
(15) a group of the formula

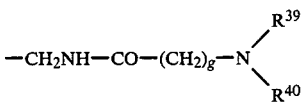

wherein g is an integer of 1 to 5 and $R^{39}$ and $R^{40}$ are each hydrogen or a lower alkyl, and
(16) a group of the formula

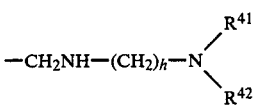

wherein h is an integer of 1 to 5 and $R^{41}$ and $R^{42}$ are each hydrogen or a lower alkyl,
or a pharmaceutically acceptable salt thereof.

The compound of the invention is called as the first compound group when W in the formula (I) is the group of —COR and as the second compound group when W is the group of X.

The invention also relates to a process for the preparation of the compounds of the formula (I) and pharmacologically acceptable salts thereof, and a pharmaceutical composition containing the formula (I) compound.

The term "lower alkyl group" as used in the definition of $R^1$ through $R^{18}$ and $R^{21}$ through $R^{42}$ in the formula (I) means both straight-chain and branched alkyl groups having 1 to 6 carbon atoms, such as methyl, ethyl, n-propyl, isopropyl, n-butyl isobutyl, 1-methypropyl, tert-butyl, n-pentyl, 1-ethylpropyl, isoamyl, and n-hexyl. The term "halogen" as used herein means chlorine, bromine, iodine and fluorine. The compounds of the present invention in which (1) the pair A and B and/or (2) the pair Y and Z together form a double bond between the associated adjacent carbon atoms can exist in the form of various stereoisomers, and these stereoisomers are also included within the scope of the present invention.

The compounds (I) of the present invention may form salts depending on the identity of the substituent W. In appropriate cases, the compounds of the present invention can be easily reacted with a pharmacologically acceptable organic or inorganic acid to form acid addition salts. Examples of such inorganic acids are hydrochloric acid, hydrobromic acid, hydriodic acid and sulfuric acid. Examples of such organic acids are maleic acid, fumaric acid, succinic acid, acetic acid, malonic acid, citric acid and benzoic acid.

Examples of typical compounds of the first compound group according to the invention are listed below.

N-(3,7,11,15-tetramethyl-2,6,10,14-hexadecatetraenoyl)-ethanolamine,
N-(3,7,11,15-tetramethyl-2,6,10,14-hexadecatetraenoyl)-propanolamine,
N-(3,7,11,15-tetramethyl-2,6,10,14-hexadecatetraenoyl)-butyl alcoholamine,
N-(3,7,11,15-tetramethyl-2,6,10,14-hexadecatetraenoyl)-amyl alcoholamine,
N-(3,7,11,15-tetramethyl-2,6,10,14-hexadecatetraenoyl)-hexyl alcoholamine,
N-methyl-N-(3,7,11,15-tetramethyl-2,6,10,14-hexadecatetraenoyl)-ethanolamine,
N-methyl-N-(3,7,11,15-tetramethyl-2,6,10,14-hexadecatetraenoyl)-propanolamine,
N-ethyl-N-(3,7,11,15-tetramethyl-2,6,10,14-hexadecatetraenoyl)-ethanolamine,
N-ethyl-N-(3,7,11,15-tetramethyl-2,6,10,14-hexadecatetraenoyl)-propanolamine,
N-(3,7,11,15-tetramethyl-2,6,10,14-hexadecatetraenoyl)-diethanolamine,
N-(3,7,11,15-tetramethyl-2,6,10,14-hexadecatetraenoyl)-dipropanolamine,
N-(3,7,11,15-tetramethyl-2,6,10,14-hexadecatetraenoyl)-N-β-hydroxyethyl-propanolamine,
N-(3,7,11,15-tetramethyl-2,6,10,14-hexadecatetraenoyl)-glycine,
N-(3,7,11,15-tetramethyl-2,6,10,14-hexadecatetraenoyl)-glycine ethyl ester,
N-(3,7,11,15-tetramethyl-2,6,10,14-hexadecatetraenoyl)-glycine propyl ester,
N-(3,7,11,15-tetramethyl-2,6,10,14-hexadecatetraenoyl)-glycine allyl ester, 3-(3,7,11,15-tetramethyl-2,6,10,14-hexadecatetraenoylamino)-1-ethylpiperidine,
2-(3,7,11,15-tetramethyl-2,6,10,14-hexadecatetraenoylaminomethyl)-1-ethylpyrrolidine,
N-(3,7,11,15-tetramethyl-2,6,10,14-hexadecatetraenoyl)-ethylenediamine,
N-(3,7,11,15-tetramethyl-2,6,10,14-hexadecatetraenoyl)-ethylenediamine hydrochloride,
N-(3,7,11,15-tetramethyl-2,6,10,14-hexadecatetraenoyl)-N',N'-dimethylethylenediamine,
N-(3,7,11,15-tetramethyl-2,6,10,14-hexadecatetraenoyl)-N',N'-diethylethylenediamine,
N-(3,7,11,15-tetramethyl-2,6,10,14-hexadecatetraenoyl)-N'-methyl-N'-ethylethylenediamine,
N-(3,7,11,15-tetramethyl-2,6,10,14-hexadecatetraenoyl)-N',N'-dimethyl-1,3-diaminopropane,
N-(3,7,11,15-tetramethyl-2,6,10,14-hexadecatetraenoyl)-N',N'-diethyl-1,3-diaminopropane,
N-(3,7,11,15-tetramethyl-2,6,10,14-hexadecatetraenoyl)-N'-methyl-N'-ethyl-1,3-diaminopropane,
N-(3,7,11,15-tetramethyl-2,6,10,14-hexadecatetraenoyl)-N',N',N'-trimethylethylenediamine chloride,
N-(3,7,11,15-tetramethyl-2,6,10,14-hexadecatetraenoyl)-N',N',N'-trimethylethylenediamine iodide,
N-(3,7,11,15-tetramethyl-2,6,10,14-hexadecatetraenoyl)-N',N',N'-triethylethylenediamine chloride,
N-(3,7,11,15-tetramethyl-2,6,10,14-hexadecatetraenoyl)-N',N',N'-triethylethylenediamine iodide,
1-(3,7,11,15-tetramethyl-2,6,10,14-hexadecatetraenoyl)-4-methylpiperazine,
1-(3,7,11,15-tetramethyl-2,6,10,14-hexadecatetraenoyl)-4-ethylpiperazine,
1-(3,7,11,15-tetramethyl-2,6,10,14-hexadecatetraenoyl)-4-propylpiperazine,
1-(3,7,11,15-tetramethyl-2,6,10,14-hexadecatetraenoyl)-4-methyl-hexahydro-1,4-diazepine,
1-(3,7,11,15-tetramethyl-2,6,10,14-hexadecatetraenoyl)-4-ethyl-hexahydro-1,4-diazepine,
1-(3,7,11,15-tetramethyl-2,6,10,14-hexadecatetraenoyl)-4-propyl-hexahydro-1,4-diazepine,
1-(3,7,11,15-tetramethyl-2,6,10,14-hexadecatetraenoyl)-4,4-dimethylpiperazine chloride,
1-(3,7,11,15-tetramethyl-2,6,10,14-hexadecatetraenoyl)-4,4-diethylpiperazine chloride,
N-(3,7,11,15-tetramethyl-2,6,10,14-hexadecatetraenoyl)-3-hydroxypiperidine,
N-(3,7,11,15-tetramethyl-2,6,10,14-hexadecatetraenoyl)-2-hydroxymethylpiperidine,
N-(3,7,11,15-tetramethyl-2,6,10,14-hexadecatetraenoyl)-3-(dimethylamino)-piperidine,
N-(3,7,11,15-tetramethyl-2,6,10,14-hexadecatetraenoyl)-3-(diethylamino)-piperidine,
N-(3,7,11,15-tetramethyl-2,6,10,14-hexadecatetraenoyl)-2-(dimethylaminomethyl)-piperidine,
N-(3,7,11,15-tetramethyl-2,6,10,14-hexadecatetraenoyl)-2-(diethylaminomethyl)-piperidine,
N-(3,7,11,15-tetramethyl-hexadecanoyl)-ethanolamine,
N-(3,7,11,15-tetramethyl-hexadecanoyl)-propanolamine,
N-(3,7,11,15-tetramethyl-hexadecanoyl)-diethanolamine,
N-(3,7,11,15-tetramethyl-hexadecanoyl)-glycine,
N-(3,7,11,15-tetramethyl-hexadecanoyl)-ethylenediamine,
N-(3,7,11,15-tetramethyl-hexadecanoyl)-ethylenediamine hydrochloride,
N-(3,7,11,15-tetramethyl-hexadecanoyl)-N'-N'-dimethylethylenediamine,
N-(3,7,11,15-tetramethyl-hexadecanoyl)-N',N',N'-trimethylethylenediamine chloride,
N-(3,7,11,15-tetramethyl-hexadecanoyl)-3-hydroxypiperidine,
N-(3,7,11,15-tetramethyl-hexadecanoyl)-2-hydroxymethylpiperidine,
N-(3,7,11,15-tetramethyl-hexadecanoyl)-3-(dimethylamino)-piperidine,
N-(3,7,11,15-tetramethyl-hexadecanoyl)-2-(dimethylaminomethyl)-piperidine,
1-(3,7,11,15-tetramethyl-hexadecanoyl)-4-methylpiperazine,
1-(3,7,11,15-tetramethyl-hexadecanoyl)-4-methyl-hexahydro-1,4-diazepine,
N-methyl-N-(3,7,11,15-tetramethyl-hexadecanoyl)-ethanolamine,
3-(3,7,11,15-tetramethyl-hexadecanoylamino)-1-ethylpiperidine,
2-(3,7,11,15-tetramethyl-hexadecanoylaminomethyl)-1-ethylpyrrolidine,
N-(3,7,11,15-tetramethyl-2-hexadecenoyl)-ethanolamine,
N-(3,7,11,15-tetramethyl-2-hexadecenoyl)-propanolamine,
N-(3,7,11,15-tetramethyl-2-hexadecenoyl)-diethanolamine,
N-(3,7,11,15-tetramethyl-2-hexadecenoyl)-glycine,
N-(3,7,11,15-tetramethyl-2-hexadecenoyl)-ethylenediamine,
N-(3,7,11,15-tetramethyl-2-hexadecenoyl)-ethylenediamine hydrochloride,
N-(3,7,11,15-tetramethyl-2-hexadecenoyl)-N',N'-dimethylethylenediamine,
N-(3,7,11,15-tetramethyl-2-hexadecenoyl)-N',N',N'-trimethylethylenediamine chloride,
N-(3,7,11,15-tetramethyl-2-hexadecenoyl)-3-hydroxypiperidine,
N-(3,7,11,15-tetramethyl-2-hexadecenoyl)-2-hydroxymethylpiperidine,
N-(3,7,11,15-tetramethyl-2-hexadecenoyl)-3-(dimethylamino)-piperidine,
N-(3,7,11,15-tetramethyl-2-hexadecenoyl)-2-(dimethylaminomethyl)-piperidine,
1-(3,7,11,15-tetramethyl-2-hexadecenoyl)-4-methylpiperidine,
1-(3,7,11,15-tetramethyl-2-hexadecenoyl)-4-methyl-hexahydro-1,4-diazepine,
N-methyl-N-(3,7,11,15-tetramethyl-2-hexadecenoyl)-ethanolamine,
3-(3,7,11,15-tetramethyl-2-hexadecenoylamino)-1-ethylpiperidine,
2-(3,7,11,15-tetramethyl-2-hexadecenoylaminomethyl)-1-ethylpyrrolidine,
N-(3,7,11,15-tetramethyl-6,10,14-hexadecatrienoyl)-ethanolamine,
N-(3,7,11,15-tetramethyl-6,10,14-hexadecatrienoyl)-propanolamine,
N-(3,7,11,15-tetramethyl-6,10,14-hexadecatrienoyl)-diethanolamine,
N-(3,7,11,15-tetramethyl-6,10,14-hexadecatrienoyl)-glycine,
N-(3,7,11,15-tetramethyl-6,10,14-hexadecatrienoyl)-ethylenediamine,
N-(3,7,11,15-tetramethyl-6,10,14-hexadecatrienoyl)-ethylenediamine hydrochloride,
N-(3,7,11,15-tetramethyl-6,10,14-hexadecatrienoyl)-N',N'-dimethylethylenediamine, N-(3,7,11,15-tetramethyl-6,10,14-hexadecatrienoyl)-N',N',N'-trimethylethylenediamine chloride,
N-(3,7,11,15-tetramethyl-6,10,14-hexadecatrienoyl)-3-hydroxypiperidine,
N-(3,7,11,15-tetramethyl-6,10,14-hexadecatrienoyl)-2-hydroxymethylpiperidine,
N-(3,7,11,15-tetramethyl-6,10,14-hexadecatrienoyl)-3-(dimethylamino)-piperidine,
N-(3,7,11,15-tetramethyl-6,10,14-hexadecatrienoyl)-2-(dimethylaminomethyl)-piperidine,
1-(3,7,11,15-tetramethyl-6,10,14-hexadecatrienoyl)-4-methylpiperazine,
1-(3,7,11,15-tetramethyl-6,10,14-hexadecatrienoyl)-4-methyl-hexahydro-1,4-diazapine,
N-methyl-N-(3,7,11,15-tetramethyl-6,10,14-hexadecatrienoyl)-ethanolamine,
3-(3,7,11,15-tetramethyl-6,10,14-hexadecatrienoylamino)-1-ethylpiperidine,
2-(3,7,11,15-tetramethyl-6,10,14-hexadecatrienoylaminomethyl)-1-ethylpyrrolidine,
N-(3,7,11-trimethyl-2,6,10-dodecatrienoyl)-ethanolamine,
N-(3,7,11-trimethyl-2,6,10-dodecatrienoyl)-propanolamine,
N-(3,7,11-trimethyl-2,6,10-dodecatrienoyl)-diethanolamine,
N-(3,7,11-trimethyl-2,6,10-dodecatrienoyl)-glycine,
N-(3,7,11-trimethyl-2,6,10-dodecatrienoyl)-ethylenediamine,
N-(3,7,11-trimethyl-2,6,10-dodecatrienoyl)-ethylenediamine hydrochloride,
N-(3,7,11-trimethyl-2,6,10-dodecatrienoyl)-N',N'-dimethylethylenediamine,
N-(3,7,11-trimethyl-2,6,10-dodecatrienoyl)-N',N',N'-trimethylethylenediamine chloride,
N-(3,7,11-trimethyl-2,6,10-dodecatrienoyl)-3-hydroxypiperidine,
N-(3,7,11-trimethyl-2,6,10-dodecatrienoyl)-2-hydroxypiperidine,
N-(3,7,11-trimethyl-2,6,10-dodecatrienoyl)-3-dimethylamino-piperidine,
N-(3,7,11-trimethyl-2,6,10-dodecatrienoyl)-2-dimethylaminomethyl-piperidine,
1-(3,7,11-trimethyl-2,6,10-dodecatrienoyl)-4-methylpiperazine,
1-(3,7,11-trimethyl-2,6,10-dodecatrienoyl)-4-methyl-hexahydro-1,4-diazepine,
N-methyl-N-(3,7,11-trimethyl-2,6,10-dodecatrienoyl)-ethanolamine,
3-(3,7,11-trimethyl-2,6,10-dodecatrienoylamino)-1-ethylpiperidine,
2-(3,7,11-trimethyl-2,6,10-dodecatrienoylaminomethyl)-1-ethylpyrrolidine,
N-(3,7,11,15,19-pentamethyl-2,6,10,14,18-eicosapentaenoyl)-ethanolamine,
N-(3,7,11,15,19-pentamethyl-2,6,10,14,18-eicosapentaenoyl)-propanolamine,
N-(3,7,11,15,19-pentamethyl-2,6,10,14,18-eicosapentaenoyl)-diethanolamine,
N-(3,7,11,15,19-pentamethyl-2,6,10,14,18-eicosapentaenoyl)-glycine,
N-(3,7,11,15,19-pentamethyl-2,6,10,14,18-eicosapentaenoyl)-ethylenediamine,
N-(3,7,11,15,19-pentamethyl-2,6,10,14,18-eicosapentaenoyl)-ethylenediamine hydrochloride,
N-(3,7,11,15,19-pentamethyl-2,6,10,14,18-eicosapentaenoyl)-N',N'-dimethylethylenediamine,
N-(3,7,11,15,19-pentamethyl-2,6,10,14,18-eicosapentaenoyl)-N',N',N'-trimethylethylenediamine chloride,
N-(3,7,11,15,19-pentamethyl-2,6,10,14,18-eicosapentaenoyl)-3-hydroxypiperidine,
N-(3,7,11,15,19-pentamethyl-2,6,10,14,18-eicosapentaenoyl)-2-hydroxymethylpiperidine,
N-(3,7,11,15,19-pentamethyl-2,6,10,14,18-eicosapentaenoyl)-3-dimethylaminopiperidine,
N-(3,7,11,15,19-pentamethyl-2,6,10,14,18-eicosapentaenoyl)-2-dimethylaminomethylpiperidine,
N-(3,7,11,15,19-pentamethyl-2,6,10,14,18-eicosapentaenoyl)-3-diethylaminopiperidine,
N-(3,7,11,15,19-pentamethyl-2,6,10,14,18-eicosapentaenoyl)-2-diethylaminomethylpiperidine,
1-(3,7,11,15,19-pentamethyl-2,6,10,14,18-eicosapentaenoyl)-4-methylpiperazine,
1-(3,7,11,15,19-pentamethyl-2,6,10,14,18-eicosapentaenoyl)-4-methyl-hexahydro-1,4-diazepine,
N-methyl-N-(3,7,11,15,19-pentamethyl-2,6,10,14,18-eicosapentaenoyl)-ethanolamine,
3-(3,7,11,15,19-pentamethyl-2,6,10,14,18-eicosapentaenoylamino)-1-ethylpiperidine,
and
2-(3,7,11,15,19-pentamethyl-2,6,10,14,18-eicosapentenoylaminomethyl)-1-ethylpyrrolidine.

Examples of typical compounds of the second compound group according to the invention are listed below.

1. 2-palmitoylamino-2-ethyl-1,3-propanediol
2. 2-oleoylamino-2-ethyl-1,3-propanediol
3. 2-(3',7',11',15'-tetramethyl-hexadecanoylamino)-1-ethyl-piperidine
4. 2-(3',7',11',15'-tetramethyl-2'-hexadecaenoylamino)-1-ethyl-piperidine
5. 2-(3',7',11',15'-tetramethyl-hexadecanoylaminomethyl)-1-ethyl-pyrrolidine
6. 2-(3',7',11',15'-tetramethyl-2'-hexadecaenoylaminomethyl)-1-ethyl-pyrrolidine
7. N-(3,7,11,15-tetramethyl-hexadecanoylaminoethyl)-pirrolidine
8. N-3,7,11,15-tetramethyl-2-hexadecaenoylaminoethyl)-pirrolidine
9. N-(3,7,11-trimethyl-2,6,10-dodecatrienoylaminoethyl)-morpholine
10. N-(3,7,11,15-tetramethyl-hexadecanoylaminoethyl)-morpholine
11. N-(3,7,11,15-tetramethyl-hexadecanoyl)-N',N'-dimethyl-ethylenediamine hydrochloride
12. N-(3,7,11,15-tetramethyl-hexadecanoyl)-N',N'-diisopropyl-ethylenediamine hydrochloride
13. N-(3,7,11,15-tetramethyl-2,6,10,14-hexadecatetraenoyl)-N',N',-diisopropyl-ethylenediamine hydrochloride
14. N-(3,7,11,15-tetramethyl-2,6,10,14-hexadecatetraenoyl)-N',N'-diethyl-ethylenediamine hydrochloride
15. N-(3,7,11,15-tetramethyl-hexadecanoyl)-N',N'-diethyl-ethylenediamine
16. N-(3,7,11,15-trimethyl-2,6,10-dodecatrienoyl)-N',N'-diethyl-ethylenediamine
17. N'-(3,7,11-trimethyl-2,6,10-dodecatrienoyl)-2-aminopyridine
18. N'-(3,7,11,15-tetramethyl-2,6,10,14-hexadecatetraenoyl)-2-aminopyridine
19. N-(3,7,11-trimethyl)-2,6,10-dodecatrienoyl)-imidazole
20. N-(3,7,11,15-tetramethyl-hexadecanoyl)-imidazole
21. N-3',7',11'-trimethyl-2',6',10',-dodecatrienoyl-2-amino-2-ethyl-1,3-propanediol 22. N-(3',7',11',15'-tetramethyl-hexadecanoyl)-2-amino-2-ethyl-1,3-propanediol
23. N-(3',7',11',15'-tetramethyl-hexadecanoyl)-3-amino-1,2-propanediol
24. N-(3',7',11'-trimethyl-2',6',10'-dodecatrienoyl)-3-amino-1,2-propanediol
25. N-(3,7,11,15-tetramethyl-2,6,10,14-hexadecatetraenoil)-N',N',N'',N''-tetraethyl-diethylenetriamine
26. N-(3,7,11,15-tetramethyl-2,6,10,14-hexadecatetraenoil)-N',N',N'',N''-tetraisopropyl-diethylenetriamine
27. N-(3,7,11,15-tetramethyl-hexadecanoil)-N',N',N'',N''-tetramethyl-diethylenetriamine
28. N-(3,7,11-trimethyl-2,6,10-dodecatrienoil)-N',N',N'',N''-tetramethyl-diethylenetriamine
29. N-(3,7,11,15-tetramethyl-2,6,10,14-hexadecatetraenoil)-N',N',N'',N''-tetraisopropyl-diethylenetriamine hydrochloride
30. N-(3,7,11,15-tetramethyl-hexadecanoil)-N',N',N'',N''-tetramethyl-diethylenetriamine hydrochloride
31. N-(3,7,11-trimethyl-2,6,10-dodecatrienoil)-N',N',N'',N''-tetramethyl-diethylenetriamine hydrochloride
32. N-(3,7,11,15-tetramethyl-2,6,10,14-hexadecatetraenyl)-N',N'-diethylaminomethyl)-carboxamide
33. N-(3,7,11,15-tetramethyl-2-hexadecaenyl)-N',N'-dimethylaminomethyl-carboxamide
34. N-(3,7,11-trimethyl-2,6,10-dodecatrienyl)-N',N'-diethylaminomethyl-carboxamide
35. N-(3,7,11,15-tetramethyl-hexadecyl)-2-aminoethyl-carboxamide
36. N-(3,7,11-tetramethyl-2,6,10-dodecatrienyl)-2-aminoethyl-carboxamide
37. N-(3,7,11,15-tetramethyl-hexadecyl)-N',N'-dimethylethylenediamine
38. N-(3,7,11,15-tetramethyl-2,6,10,14-hexadecatetraenyl)-N',N'-diethyl-ethylenediamine
39. N-(4-(2',6',10'-trimethyl 1',5',9'-undecatrienyl)benzoyl)-propanolamine
40. N-(4-(2',6'-dimethyl-1',5'-heptadienyl)-bezoyl)-ethanolamine
41. N-(4-(2',6',10'-trimethyl-1',5',9'-undecatrienyl)-benzoyl)-dipropanolamine
42. N-(4-(2',6'-dimethyl-1',5'-heptadienyl)-benzoyl)-diethanolamine
43. N-(4-(2',6',10'-trimethyl-1',5',9'-undecatrienyl)-benzoyl)-N',N'-diethylethylenediamine
44. N-(4-(2',6',10'-trimethyl-1',5',9'-undecatrienyl)-benzoyl)-N',N'-diisopropylethylenediamine
45. N-(4-(2',6',10'trimethyl-1',5',9'-undecatrienyl)-benzoyl)-N',N'-diethylethylenediamine hydrochloride
46. N-(4-(2',6',10'-trimethyl-1',5',9'-undecatrienyl)-benzoyl)-N',N'-diisopropylethylenediamine hydrochloride
47. N-(4-(2',6',10'-trimethyl-1',5',9'-undecatrienyl)-benzoyl)-N',N',N'',N''-tetraethyl-diethylenetriamine
48. N-(4-(2',6'-dimethyl-1',5'-heptadienyl)-benzoyl)-N',N',N'',N''-tetramethyl-diethylenetriamine
49. N-(4-(2',6',10'-trimethyl-1',5',9'-undecatrienyl)-benzoyl)-N',N',N'',N''-tetraethyl-diethylenetriamine hydrochloride
50. N-(4-(2',6',10'-trimethyl-undecyl)-benzoyl)-propanolamine
51. N-(4-(2',6'-dimethyl-heptyl)-benzoyl)-diethanolamine
52. N-(4-(2',6',10'-trimethyl-undecyl)-benzoyl)-N',N'-diethylethylenediamine
53. N-(4-(2',6',10'-trimethyl-undecyl)-benzoyl)-N',N'-diethylethylenediamine hydrochloride
54. N-(4-(2',6',10'-trimethyl-undecyl)-benzoyl)-N',N',N'',N''-tetraethyl-diethylenetriamine
55. N-(4-(2',6',10'-trimethyl-undecyl)-benzoyl)-N',N',N'',N''-tetraethyl-diethylenetriamine hydrochloride
56. N-(4-(2',6'-dimethyl-1',5'-heptadienyl)-benzoyl)ethanolamine
57. N-(4-(2',6'-dimethylheptyl)-benzoyl)propanolamine
58. N-(4-(2',6'-dimethyl-1',5'-heptadienyl)-benzoyl)-N',N',N'',N''-tetramethyl-diethylenetriamine
59. N-(4-(2',6'-dimethyl-1',5'-heptadienyl)-benzoyl)-N',N',N'',N''-tetraethyl-diethylenetriamine
60. N-(4-(2',6'-dimethylheptyl)-benzoyl)-N',N',N'',N''-tetramethyl-diethylenetriamine hydrochloride
61. N-(4-(2',6',10',14'-tetramethyl-1',5',9',13'-pentadecatetraenyl)-benzoyl)-ethanolamine
62. N-(4-(2',6',10',14'-tetramethyl-pentadecyl)-benzoyl)-propanolamine
63. N-(4-(2',6',10',14'-tetramethyl-1',5',9',13'-pentadecatetraenyl)-benzoyl)-N',N',N'',N''-tetramethyl-diethylenetriamine
64. N-(3-(4'-(4'',8''-dimethyl-3'',7''-nonadienyl)phenyl)-butanoyl)ethanolamine
65. N-(3-(4'-(4'',8''-dimethyl-3'',7''-nonadienyl)phenyl)-butanoyl)-N',N',N'',N''-tetramethyl-diethylenetriamine
66. N-(3-(4'-(4'',8''-dimethyl-3'',7''-nonadienyl)-phenyl)-2-butenoyl)ethanolamine
67. N-(3-(4'-(4'',8''-dimethyl-3'',7''-nonadienyl)-phenyl)-2-butenoyl)-N',N',N'',N''-tetramethyl-diethylenetriamine
68. N-(2-methyl-4-(2',6',10'-trimethyl-1',5',9'-undecatrienyl)-benzoyl)ethanolamine
69. N-(2-methyl-4-(2',6',10'-trimethyl-1',5',9'-undecatrienyl)-benzoyl)-N',N',N'',N''-tetramethyl-diethylenetriamine
70. N-(2-floro-4-(2',6',10'-trimethyl-1',5',9'-undecatrienyl)-benzoyl)-ethanolamine
71. N-(2-floro-4-(2',6',10'-trimethyl-1',5',9'-undecatrienyl)-benzoyl)-N',N',N'',N''-tetramethyl-diethylenetriamine
72. N-(4-(2',6',10'-trimethyl-1',5',9'-undecatrienyl)-1-naphthoyl)-ethanolamine
73. N-(4-(2',6',10'-trimethyl-1',5',9'-undecatrienyl)-1-naphthoyl)-N',N',N'',N''-tetraethyl-diethylenetriamine
74. N-(5-(2',6',10'-trimethyl-1',5',9'-undecatrienyl)-1-naphthoyl)ethanolamine
75. N-(5-(2',6',10'-trimethyl-1',5',9'-undecatrienyl)-1-naphthoyl)-N',N',N'',N''-tetramethyl-diethylenetriamine
76. N-(4-(2',6',10'-trimethyl-undecyl)-5,6,7,8-tetrahydro-1-naphthoyl)propanolamine
77. N-(4-(2',6',10'-trimethyl-undecyl)-5,6,7,8-tetrahydro-1-naphthoyl)-N',N',N'',N''-tetraethyl-diethylenetriamine
78. N-(4-(2',6',10'-trimethyl-1',5',9'-undecatrienyl)-5,6,7,8-tetrahydro-1-naphthoyl)ethanolamine
79. N-(4-(2',6',10'-trimethyl-1',5',9'-undecatrienyl)-5,6,7,8-tetrahydro-1-naphthoyl)-N',N',N'',N'''-tetramethyl-diethylenetriamine The polyprenyl compound according to the invention have excellent anti-PAF and antithrombic activities, and are useful in pharmaceutical compositions intended for utilizing these anti-PAF and antithrombic activities. The term "PAF" means platelet activating factor. Barbaro et al found in 1966 that a rabbit basophile sensitized by immunoglobulin E (IgE) released a factor which caused platelet degranulation and aggregation. This factor was named PAF by Benveniste et al in 1972. Demopoulos et al reported in 1979 that its structure was identical with that of 1-alkyl-2-acetyl-sn-glycero-3-phosphocholine. PAF is an alkyl ether phospholipid having an acetyl group which is a new mediator for platelet aggregation.

Human disseminated intravascular coagulation syndrome (DIC) is a condition wherein blood coagulation is abnormally promoted, blood in the microcardiovascular system is widely coagulated and many thrombi are formed. One of the factors causing this condition is thrombin. As noted above, the compounds of the present invention have antithrombic and anti-PAF activity. Therefore, the compounds of the present invention are useful as excellent antithrombic drugs having both antithrombic and anti-PAF activities for the treatment of DIC.

The formation of thrombi can further cause hemadostenosis, angiostenosis and ischemic lesions or infarctions in principal internal organs such as heart, brain and lungs. Therefore, the compounds of the present invention are useful for the therapy and prophylaxis of myocardial angina pectoris, cerebral thrombosis, DIC and chronic arteriosclerosis. In addition to being useful as drugs for the therapy and prophylaxis of these thromboses, the compounds of the present invention having anti-PAF activity can be used as anti-inflammatory drugs, antiasthmatic drugs, antiarteriosclerotic drugs, antishock and blood pressure controlling drugs, immune function controlling drugs and antiallergic drugs.

We have unexpectedly found that the compounds of the present invention have anti-PAF and antithrombic activities. The present invention is based on this finding. No compounds similar in structure to those of the present invention have been known to exhibit an anti-PAF activity.

The first compound group according to the invention wherein W in the formula (I) is the group of —COR can be produced by various methods. For example a polyprenyl carboxylic acid of the formula (II)

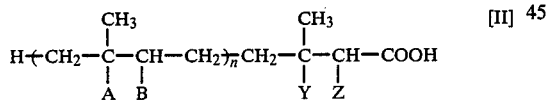

wherein A, B, Y, Z and n have the same meanings as defined above, or a reactive derivative thereof, is reacted with an amine of the formula RH [III], wherein R has the same meaning as defined above, to amidate said carboxylic acid or its derivative, thus producing the desired polyprenylcarboxylic acid amide [I]. Examples of reactive derivatives of the carboxylic acid [II] include halides, anhydrides and mixed anhydrides of the acid [II].

If desired, the reaction can be carried out in the presence of a dehydrating agent such as N,N'-dicyclohexylcarbodiimide, N,N'-diethylcarbodiimide, trialkyl phosphate, ethyl polyphosphate or tosyl chloride, in order to conduct the reaction smoothly. Further, in order to capture the hydrogen halide formed by the reaction and promote the reaction, a base can be added. Examples of such bases include inorganic bases, such as potassium hydroxide, sodium hydroxide, potassium carbonate and sodium carbonate, and tertiary amines, such as pyridine and triethylamine. The reaction can ordinarily be conducted in a solvent, such as dioxane, tetrahydrofuran, dimethyl sulfoxide or a lower alcohol, or mixtures thereof.

The second compound group according to the invention wherein W in the formula (I) is X can be produced by various preparation methods. Some examples therefor are described below.

(1) When X is one of the groups (6) to (14) defined hereinbefore, the following preparation may be used.

The intended product can be obtained by reacting a polyprenyl carboxylic acid of the formula (II)

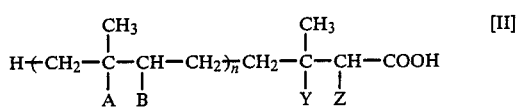

wherein A, B, Y and Z are defined hereinbefore and n is an integer of 1 to 3, or a reactive derivative thereof, with one of amine compounds of the formulae:

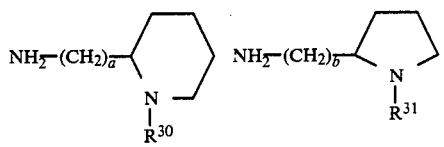

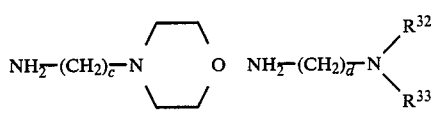

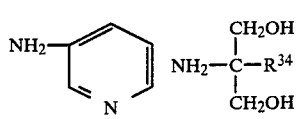

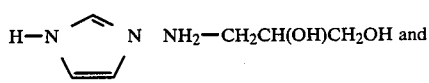

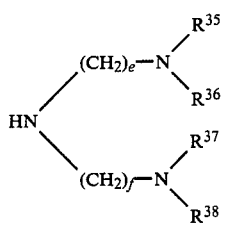

Also in these preparation methods, the reactive derivative, a dehydrating agent, a base and a solvent may be used in the same manner as described hereinbefore.

(2) When X is the group (15), the product can be obtained by reacting a polyprenyl compound of the formula (IV)

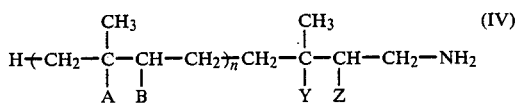

wherein A, B, Y, Z and n are defined hereinbefore, with a carboxylic acid of the formula (V)

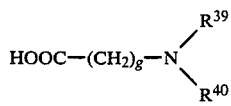  (V)

in the same manner as shown in the before mentioned (1) to carry our amidation.

(3) When X is the group (16), the product can be obtained by reacting a halide of a polyprenyl compound of the formula (VI)

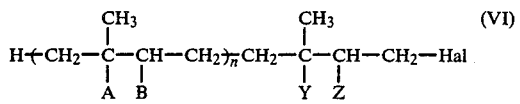  (VI)

wherein Hal is a halogen and A, B, Y, Z and n are defined hereinbefore, with an amine compound of the formula (VII) in order to effect dehalogenation.

  (VII)

(4) When X is the group (1), the product can be obtained by reacting a polyprenyl compound of the formula (VII)

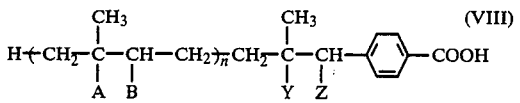  (VIII)

with, for example, a thionyl chloride in order to produce an acid halide of the formula (IX)

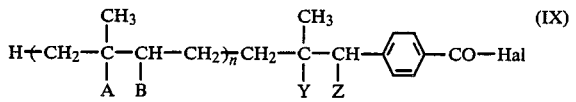  (IX)

and then reacting the resulting acid halide with an amine compound of the formula (X): $R^{22}H$ in order to produce the intended product.

(5) When X is the group (2), the intended product can be obtained by reacting a polyprenyl compound of the formula (XI)

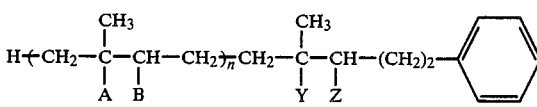  (XI)

with, for example, thionyl chloride to give an acid halide of the formula (XII)

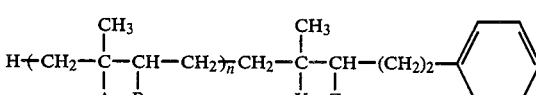  (XII)

wherein Hal is a halogen, and then reacting the acid halide with an amine compound of the formula (X): $R^{22}H$.

(6) When X is one of the groups (3), (4) and (5), the product can be obtained by reacting a polyprenyl compound of each of the formulae (XIV), (XV) and (XVI)

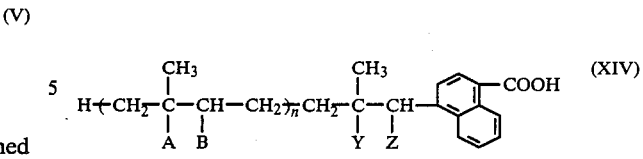  (XIV)

(XV)

(XVI)

with, for example, thionyl chloride in order to give an acid halide of each polyprenyl compound and then reacting the resultant with an amine compound of the formula (X).

In the preparation methods as mentioned above, oxalyl chloride maybe replaced for thionyl chloride.

The following experimental example is provided to illustrate the effects of the compounds according to the invention.

EXPERIMENTAL EXAMPLE (1) Anti-PAF activity

Experimental method (a) Preparation of washed platelet suspension (hereinafter referred to as W.P.)

A blood sample was collected from a carotid artery of a male rabbit weighing 2.5 kg, while adding thereto one volume of a 3.13% sodium citrate solution per 9 volumes of blood as a coagulant. The resulting blood was centrifuged at 200 xg for 20 minutes to separate out platelet-rich plasma (hereinafter referred to as PRP). This PRP was centrifuged at 1,000 xg for 15 minutes to separate the platelets from the plasma. The deposited platelets were washed twice with a Tyrode solution (Tyrode-$Ca^{++}$), from which $Ca^{++}$ had been removed and to which 1% bovine serum albumin (BSA) had been added, such that $9 \times 10^5$ platelets per $\mu l$ were finally suspended in the Tyrode solution.

(b) Preparation of specimens and PAF

Specimens were dissolved or suspended in a physiological saline. PAF was dissolved in a Tyrode solution containing 1% BSA. PAF synthesized from D-mannitol in accordance with a method disclosed by J. J. Godfroid et al was used (FEBS Letters 116, 161–164, 1980).

(c) Measurement of platelet aggregation

Platelet aggregation measurements were conducted according to nephelometry described by Born et al using a platelet aggregation meter manufactured by Schenko Co. Specimen solutions having various concentrations of test compounds and 0.25 ml of W.P. were subjected to preincubation at 37° C. for 4 minutes, and then PAF was added thereto to give a final PAF concentration of 30 ng/ml to provoke platelet aggregation. The transmittance of the W.P. before aggregation, that is, before the addition of the aggregation provoking agent, was rated as 0, and the transmittance of the Tyrode solution was rated as 100. After the addition of the PAF solution to the W.P., light transmittance increased as aggregation proceeded. The value of the light transmittance at the time when the aggregation had proceeded to a maximum was rated as the maximum aggregation (hereinafter referred to as MA) which was used as an index of the degree of aggregation.

The inhibition rate was calculated according to the following equation. The aggregation in a W.P.-containing physiological saline solution free of test compound, as a control, was rated as 0% aggregation inhibition.

Aggregation inhibition rate (%) =

$$\frac{M.A.\ Control - M.A.\ Sample}{M.A.\ Control} \times 100$$

wherein
 M.A. Control: maximum aggregation after platelet aggregation in PAF was provoked, after the addition of physiological saline.
 M.A. Sample: maximum aggregation after platelet aggregation in PAF was provoked, after the addition of the test compound.

(2) Antithrombic activity

The measurement of the antithrombic activity was conducted in the same manner as described above, except that bovine thrombin at a final concentration of 0.2 units/ml was used as the platelet aggregation provoking agent in place of PAF.

The results are shown in Table 1.

TABLE 1

| Compound | Concentration (μM) | Inhibition rate PAF (%) | Inhibition rate Thrombin (%) |
|---|---|---|---|
| H−(structure)₃−C(=O)−NHCH₂CH₂OH | 50 | 50 | — |
| H−(structure)₃−C(=O)−NHCH₂CH₂CH₂OH | 50 | 22.1 | 11.6 |
| H−(structure)₃−C(=O)−N(CH₃)−CH₂CH₂OH | 50 | 16.3 | 3.9 |
| H−(structure)₃−C(=O)−NHCH₂CH₂NH₂ | 50 | 80.8 | — |
| H−(structure)₃−C(=O)−NHCH₂CH₂N(CH₃)₂ | 50 | 90.8 | 70.5 |
| H−(structure)₃−C(=O)−N(piperazine)−N−CH₃ | 50 | 51.2 | 43.3 |
| H−(structure)₃−C(=O)−N(homopiperazine)−N−CH₃ | 50 | 93.1 | 83.7 |
| H−(structure)₃−C(=O)−NHCH₂CH₂−N⁺(CH₃)₃·I⁻ | 50 | 100 | 92 |
| H−(structure)₃−C(=O)−NHCH₂CH₂−N⁺(CH₃)₃·Cl⁻ | 50 | 93.9 | 86.5 |

TABLE 1-continued
| Compound | Concentration (μM) | Inhibition rate PAF (%) | Inhibition rate Thrombin (%) |
|---|---|---|---|
| 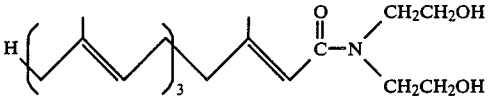 | 50 | 76.4 | — |
| 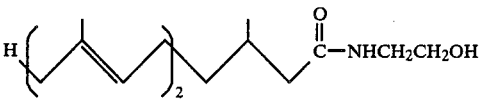 | 50 | 31.4 | — |
| 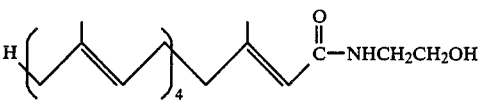 | 50 | 22.7 | — |
| 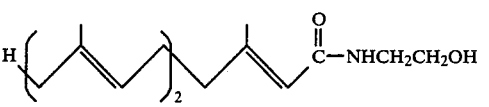 | 50 | 18.7 | — |
| 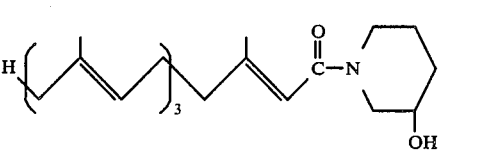 | 50 | 27.4 | 19.2 |
| 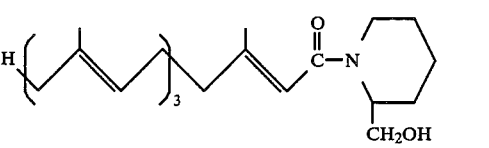 | 50 | 34.4 | 27.4 |
| 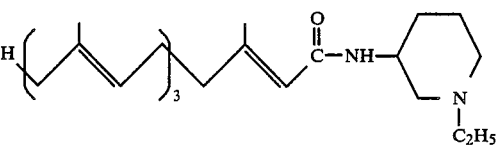 | 50 | 80.3 | 24.2 |
| 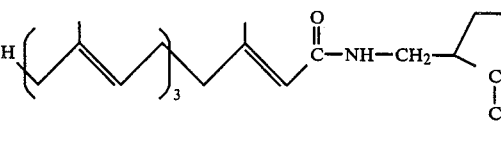 | 50 | 87.0 | 79.6 |
| 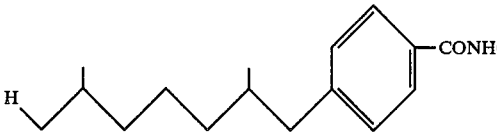 | 20 | 57.8 | |
| 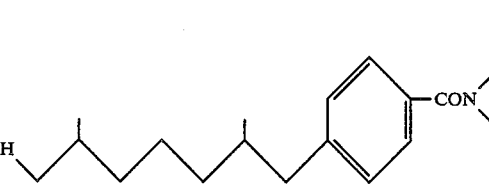 | 20 | 59.4 | |

TABLE 1-continued

| Compound | Concentration (μM) | Inhibition rate PAF (%) | Inhibition rate Thrombin (%) |
|---|---|---|---|
| [structure] | 20 | 57.8 | |
| | 50 | 82.6 | |
| [structure] | 20 | 55.9 | |
| [structure] | 20 | 63.2 | |
| | 50 | 82.2 | |
| [structure] | 20 | 50.0 | |
| [structure] | 20 | 61.4 | |
| [structure] | 20 | 64.9 | |
| [structure] | 20 | 59.3 | |

TABLE 1-continued

| Compound | Concentration (μM) | Inhibition rate PAF (%) | Inhibition rate Thrombin (%) |
|---|---|---|---|
| H-[CH₂...]₂-naphthyl-CON(CH₂CH₂N(CH₃)₂)₂ | 20 | 58.3 | |
| H-[CH₂...]₂-tetrahydronaphthyl-CON(CH₂CH₂N(CH₃)₂)₂ | 20 | 50.5 | |
| H-[...]₃-NHCOCH₂N(CH₃)₂ | 20 | 60.4 | |
| H-[...]₃-NHCOCH₂CH₂NH₂ | 20 | 59.1 | |
| H-[...]₃-NHCH₂CH₂N(CH₃)₂ | 20 | 37.1 | |
| H-[...]₃-C(O)-NHCH₂CH₂N(CH₃)₂·HCl | 20 | 74.3 | |
| H-[...]₃-C(O)-N(CH₂CH₂N(CH₃)₂)₂ | 20 | 88.7 | 76.4 |
| H-[...]₂-C₆H₄-CONHCH₂CH₂N(CH₃)₂·HCl | 20 | 73.5 | 34.2 |

TABLE 1-continued

| Compound | Concentration ($\mu$M) | Inhibition rate PAF (%) | Inhibition rate Thrombin (%) |
| --- | --- | --- | --- |
| 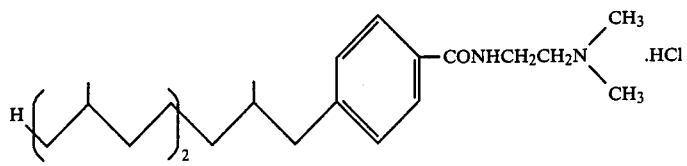 | 20 | 80.6 | 70.3 |
| 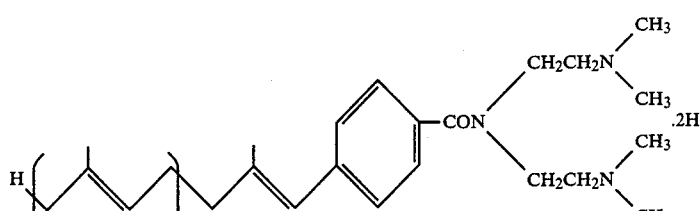 | 20 | 93.6 | 70.6 |
| 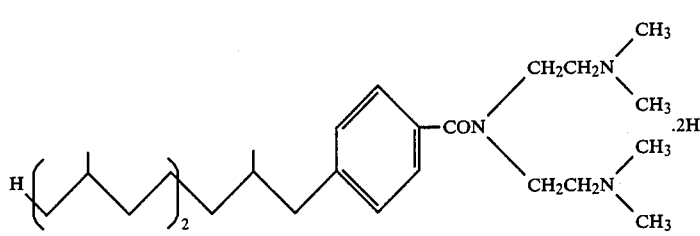 | 20 | 74.7 | 78.8 |

It is apparent from the above experimental results that the compounds of the present invention have an excellent anti-PAF activity. In addition to being useful as drugs for the prophylaxis and therapy of thromboses, the compounds of the invention are also useful as anti-inflammatory drugs, antiasthmatic drugs, antiarteriosclerotic drugs, antishock and blood pressure controlling drugs, immune function controlling drugs and antiallergic drugs.

The compounds of the present invention have a very low toxicity and high safety, and are suitable for long-term continuous administration. The present invention is very valuable in this sense. When the compounds of the present invention described in the above experimental example were orally administered in doses of 500 mg/kg to SD rats (each weighing about 200 g), no deaths or side effects were observed.

Dosages of the compounds of the present invention administered as a drug exhibiting an anti-PAF activity to human or animal patients vary greatly depending on the type and extent of the disease, the particular compound employed and the age of the patients, and, thus, the dosage amount is not particularly limited. Generally, however, the compounds of the invention are orally or parenterally administered at dosages in the range of from 10 to 1,000 mg/day/adult, preferably about 50 to 300 mg/day/adult. The unit dosage forms of drugs to be administered include powders, fine-grained powders, granules, tablets, capsules and injection liquids. Such drug forms are prepared by conventional methods using conventional pharmaceutical carriers.

In the formulation of solid preparations for oral administration, an excipient is added to a base. If desired, a binder, disintegrator, lubricant, colorant, flavoring agent, and other conventional additives are added thereto. The mixture is then shaped into powder, coated powder, granules or capsules by any conventional method.

Examples of suitable excipients are lactose, corn starch, sucrose, glucose, sorbitol, crystalline cellulose and silicon dioxide. Examples of suitable binders are polyvinyl alcohol, polyvinyl ether, ethylcellulose, methylcellulose, acacia, tragacanth, gelatin, shellac, hydroxypropylcellulose, hydroxypropylstarch and polyvinylpyrrolidone. Examples of disintegrators are starch, agar-agar, gelatin powder, crystalline cellulose, calcium carbonate, sodium hydrogencarbonate, calcium citrate, dextrin and pectin. Examples of lubricants include magnesium stearate, talc, polyethylene glycol, silica and hardened vegetable oil. As colorants, any pharmaceutically acceptable substances may be used. Examples of flavoring agents are cocoa powder, menthol, peppermint oil, borneol and cinnamon powder. The tablets and granules can be coated with sugar, gelatin or other coating agents.

In the formulation of an injection liquid, a pH adjuster, a buffer, a stabilizer, a solubilizer, etc. are added to a base to form a preparation for hypodermic, intramuscular or intravenous injection by any conventional method.

The compounds of the present invention can be administered orally or parenterally to animals such as domestic animals and poultry. Oral administration can usually be conducted by blending the compounds with ordinary feed. In parenteral administration, an injection is prepared by a conventional method and the compound is hypodermically administered, intramuscularly or intravenously, to the animal.

The following is an example of a preparation containing N-(3,7,11,15-tetramethyl-2,6,10,14-hexadecatetraenoyl)-ethanolamine, hereinafter referred to as the base, a typical compound of the present invention, as the active ingredient.

Formulation of preparation (tablet)

| | |
|---|---|
| base | 10 g |
| silicic anhydride | 50 g |
| crystalline cellulose | 70 g |
| corn starch | 36 g |
| hydroxypropylcellulose | 10 g |
| magnesium stearate | 4 g |

The above ingredients are formulated into tablets (180 mg per tablet) by a conventional method.

The following examples of preparation of compounds according to the invention are provided to illustrate the present invention, but are not to be construed as limiting the invention in any way.

EXAMPLE 1

N-(3,7,11,15-Tetramethyl-2,6,10,14-hexadecatetraenoyl)-ethanolamine 6.1 g of 3,7,11,15-tetramethyl-2,6,10,14-hexadecatetraenoic acid was dissolved in 50 ml of tetrahydrofuran and 3.1 ml of triethylamine was added thereto. While cooling the mixture in ice with stirring, 2.1 ml of ethyl chlorocarbonate was added dropwise. Then the mixture was stirred for 15 minutes and 1.8 ml of ethanolamine was added thereto. After the mixture was stirred for 30 minutes at room temperature, water was added thereto and the resulting aqueous solution was extracted with ethyl acetate. The ethyl acetate layer was separated from the aqueous layer, washed with 5% aqueous hydrochloric acid solution and then water, and dried over magnesium sulfate. The solvent was distilled off. The resulting reaction mixture was subjected to chromatography on silica gel column to afford 6.5 g (yield 94%) of the title compound as a colorless oil.

Elemental analysis for $C_{22}H_{37}NO_2$

| | C | H | N |
|---|---|---|---|
| calculated (%) | 76.03 | 10.73 | 4.03 |
| found (%) | 76.00 | 10.31 | 3.94 |

Mass (m/Z): 347 (M+)
NMR (δ, CDCl$_3$): 1.59 (9H, s), 1.68 (3H, s) 1.9–2.2 (12H), 2.12 (3H, d, J=1), 2.90 (1H, br), 3.3–3.5 (2H), 3.35–3.7 (2H), 5.06 (3H, m), 5.52 (1H, s), 5.94 (1H, br, s).

EXAMPLE 2

N-(3,7,11,15-Tetramethyl-2-hexadecenoyl)-ethanolamine

The procedure of Example 1 was repeated except that 6.2 g of 3,7,11,15-tetramethyl-2-hexadecenoic acid and 1.8 ml of ethanolamine were used as starting materials. 6.7 g (yield 95%) of the title compound was obtained as a colorless oil.

Elemental analysis for $C_{22}H_{43}NO_2$

| | C | H | N |
|---|---|---|---|
| calculated (%) | 74.73 | 12.26 | 3.96 |
| found (%) | 74.54 | 12.33 | 3.88 |

Mass (m/Z): 353 (M+)
NMR (δ, CDCl$_3$): 0.84 (12H, d, J=7), 1.0–1.5 (20H, m), 1.81 (3H, d, J=1), 2.4–2.7 (2H, m), 3.3–3.5 (2H, m), 3.6–3.8 (2H, m), 5.52 (1H, s), 5.70 (1H, br).

EXAMPLE 3

N-(3,7,11,15-Tetramethyl-hexadecanoyl)-ethanolamine 6.5 g of N-(3,7,11,15-tetramethyl-2,6,10,14-hexadecatetraenoyl)-ethanolamine obtained in Example 1 was hydrogenated in the presence of a catalyst composed of palladium on carbon in 40 ml of ethanol. The ethanol layer was then separated from the catalyst and the solvent was distilled off to afford 6.7 g (yield 94%) of the title compound as a colorless oil.

Elemental analysis for $C_{22}H_{45}NO_2$

| | C | H | N |
|---|---|---|---|
| calculated (%) | 74.30 | 12.76 | 3.94 |
| found (%) | 74.20 | 12.84 | 3.91 |

Mass (m/Z): 355 (M+)
NMR (δ, CDCl$_3$): 0.86 (15H, d, J=6), 1.0–1.5 (23H), 1.96 (2H, m), 3.3–3.8 (4H), 6.05 (1H, br).

EXAMPLE 4

N-(3,7,11,15-Tetramethyl-6,10,14-hexadecatrienoyl)-ethanolamine

The procedure of Example 1 was repeated except that 6.1 g of 3,7,11,15-tetramethyl-6,10,14-hexadecatrienoic acid and 1.8 ml of ethanolamine were used as starting materials. 6.4 g (yield 92%) of the title compound was obtained as a colorless oil.

Elemental analysis for $C_{22}H_{39}NO_2$

| | C | H | N |
|---|---|---|---|
| calculated (%) | 75.59 | 11.25 | 4.01 |
| found (%) | 75.47 | 11.39 | 4.08 |

Mass (m/Z): 349 (M+)
NMR (δ, CDCl$_3$): 0.94 (3H, d, J=5), 1.1–1.5 (3H, m), 1.60 (9H, s), 1.68 (3H, s), 1.8–2.2 (12H), 3.3–3.8 (4H, m), 4.16 (1H, br), 5.09 (3H, m), 6.72 (1H, br).

EXAMPLE 5

N-(3,7,11,15,19-Pentamethyl-2,6,10,14,18-eicosapentaenoyl)-ethanolamine

The procedure of Example 1 was repeated except that 7.4 g of 3,7,11,15,19-pentamethyl-2,6,10,14,18-eicosapentaenoic acid and 1.8 ml of ethanolamine were used as starting materials. 7.7 g (yield 93%) of the title compound as a colorless oil was obtained.

Elemental analysis for $C_{27}H_{45}NO_2$

| | C | H | N |
|---|---|---|---|
| calculated (%) | 78.02 | 10.91 | 3.37 |
| found (%) | 77.93 | 10.99 | 3.30 |

Mass (m/Z): 415 (M+)
NMR (δ, CDCl$_3$): 1.60 (12H, s), 1.68 (3H, s), 1.8–2.2 (17H), 2.14 (3H, d, J=1), 3.2–3.8 (4H), 5.08 (4H, m), 5.59 (1H, br, s), 6.26 (1H, br, t).

EXAMPLE 6

N-(3,7,11-Trimethyl-2,6,10-dodecatrienoyl)-ethanolamine

The procedure of Example 1 was repeated except that 4.7 g of 3,7,11-trimethyl-2,6,10-dodecatrienoic acid and 1.8 ml of ethanolamine were used as starting materials. 5.2 g (yield 94%) of the title compound was obtained as a colorless oil.

Elemental analysis for $C_{17}H_{29}NO_2$

|  | C | H | N |
|---|---|---|---|
| calculated (%) | 73.07 | 10.46 | 5.01 |
| found (%) | 73.00 | 10.53 | 5.06 |

Mass (m/Z): 279 (M+)

NMR ($\delta$, $CDCl_3$): 1.60 (6H, s), 1.68 (3H, s), 1.8–2.3 (8H), 2.12 (3H, s), 3.2–3.8 (4H), 4.20 (1H, br), 5.08 (2H, m), 5.60 (1H, br, s), 6.76 (1H, br).

EXAMPLE 7

N-(3,7,11,15-Tetramethyl-2,6,10,14-hexadecatetraenoyl)-diethanolamine

The procedure of Example 1 was repeated except that 6.1 g of 3,7,11,15-tetramethyl-2,6,10,14-hexadecatetraenoic acid and 2.9 ml of diethanolamine were used as starting materials. 7.0 g (yield 90%) of the title compound was obtained as a colorless oil. Elemental analysis for $C_{24}H_{41}NO_3$

|  | C | H | N |
|---|---|---|---|
| calculated (%) | 73.61 | 10.55 | 3.58 |
| found (%) | 73.52 | 10.66 | 3.51 |

Mass (m/Z): 391 (M+)

NMR ($\delta$, $CDCl_3$): 1.61 (9H, s), 1.68 (3H, s), 1.8–2.2 (12H), 2.12 (3H, d, J=2), 3.4–3.9 (8H), 4.56 (2H, br), 5.08 (3H, m), 5.88 (1H, br, s).

EXAMPLE 8

N-(3,7,11,15-Tetramethyl-2,6,10,14-hexadecatetraenoyl)-glycine

The reaction of 6.1 g of 3,7,11,15-tetramethyl-2,6,10,14-hexadecatetraenoic acid with glycine ethyl ester hydrochloride was conducted in the same manner as described in Example 1 except that 6.5 ml of triethylamine was used. Then, a solution of 2.7 g of potassium hydroxide in ethanol was added. The mixture was heated under reflux for 30 minutes. After the completion of the reaction, water was added and the obtained aqueous solution was extracted with ethyl acetate. The ethyl acetate layer was washed with water and dried over magnesium sulfate. The solvent was distilled off to afford 6.1 g (yield 85%) of the title compound as a pale brown oil.

Elemental analysis for $C_{22}H_{35}NO_3$

|  | C | H | N |
|---|---|---|---|
| calculated (%) | 73.09 | 9.76 | 3.87 |
| found (%) | 72.97 | 9.80 | 3.79 |

Mass (m/Z): 361 (M+)

NMR ($\delta$, $CDCl_3$): 1.59 (9H, s), 1.66 (3H, s), 1.7–2.2 (12H), 2.10 (3H, s), 4.02 (2H, br, d, J=5), 5.04 (3H, m), 5.60 (1H, br, s), 6.08 (1H, br), 6.37 (1H, br).

EXAMPLE 9

N-(3,7,11,15-Tetramethyl-2,6,10,14-hexadecatetraenoyl)-ethylenediamine 3.1 ml of triethylamine was added to a solution of 6.1 g of 3,7,11,15-tetramethyl-2,6,10,14-hexadecatetraenoic acid in 50 ml of tetrahydrofuran. While cooling the mixture in ice with stirring, 2.1 ml of ethyl chlorocarbonate was added dropwise and the mixture was stirred for 15 minutes. Then 2.0 ml of ethylenediamine was added thereto and the mixture was stirred for 30 minutes at room temperature. Then water was added thereto and the resulting solution was extracted with chloroform.

The chloroform layer was washed with water and dried over magnesium sulfate. The solvent was distilled off. The resulting reaction mixture was chromatographed on a silica gel column to afford 5.5 g (yield 80%) of the title compound as a pale brown oil.

Elemental analysis for $C_{22}H_{38}N_2O$

|  | C | H | N |
|---|---|---|---|
| calculated (%) | 76.25 | 11.05 | 8.08 |
| found (%) | 76.22 | 11.10 | 8.10 |

Mass (m/Z): 346 (M+)

NMR ($\delta$, $CDCl_3$): 1.56 (9H, s), 5.05 (3H, m), 1.64 (3H, s), 5.56 (1H, br, s), 1.75–2.2 (14H), 6.48 (1H, br), 2.16 (3H, d, J=1), 2.7–2.95 (2H), 3.1–3.4 (2H).

EXAMPLE 10

N-(3,7,11,15-Tetramethyl-2,6,10,14-hexadecatetraenoyl)-ethylenediamine hydrochloride Hydrogen chloride gas was passed through a methanol solution of N-(3,7,11,15-tetramethyl-2,6,10,14-hexadecatetraenoyl)-ethylenediamine obtained in Example 9. The solvent was distilled off to afford 6.1 g of the title compound as a brown oil.

Elemental analysis for $C_{22}H_{39}N_2OCl$

|  | C | H | N | Cl |
|---|---|---|---|---|
| calculated (%) | 68.99 | 10.26 | 7.32 | 9.26 |
| found (%) | 68.79 | 10.50 | 7.15 | 9.20 |

Mass (m/Z): 384 (M+, $Cl^{37}$) 382 (M+, $Cl^{35}$)

NMR ($\delta$, $CDCl_3$): 1.60 (9H, s), 1.68 (3H, s), 1.7–2.3 (15H), 2.18 (3H, d, J=1), 3.0–4.0 (4H), 5.08 (3H, m), 5.74 (1H, br), 7.80 (1H, br).

EXAMPLE 11

N-(3,7,11,15-Tetramethyl-2,6,10,14-hexadecatetraenoyl)-N',N'-dimethylethylenediamine The procedure of Example 9 was repeated except that 6.1 g of 3,7,11,15-tetramethyl-2,6,10,14-hexadecatetraenoic acid and 3.3 ml of N,N-dimethylethylene diamine were used as starting materials. 6.5 g (yield 88%) of the title compound was obtained as a pale yellow oil.

Elemental analysis for $C_{24}H_{42}N_2O$

|  | C | H | N |
|---|---|---|---|
| calculated (%) | 76.95 | 11.30 | 7.48 |
| found (%) | 76.85 | 11.31 | 7.43 |

Mass (m/Z): 374 (M+)

NMR ($\delta$, $CDCl_3$): 1.60 (9H, s), 1.68 (3H, s), 1.8–2.2 (12H), 2.24 (6H, s), 2.26 (3H, s), 2.3–2.5 (2H), 2.8–3.0 (2H), 5.10 (3H, m), 5.56 (1H, br, s), 6.14 (1H, br).

EXAMPLE 12

N-(3,7,11,15-Tetramethyl-2,6,10,14-hexadecatetraenoyl)-N',N',N'-trimethylethylenediamine chloride Chloromethane gas was passed through a solution of 6.5 g of N-(3,7,11,15-tetramethyl-2,6,10,14-hexadecatetraenoyl)-N',N'-dimethylethylenediamine obtained in Example 11, dissolved in 50 ml of benzene. The solvent was distilled off to afford 7.4 g of the title compound as a white wax.

Elemental analysis for $C_{25}H_{45}N_2OCl$

|  | C | H | N | Cl |
|---|---|---|---|---|
| calculated (%) | 70.63 | 10.67 | 6.57 | 8.34 |
| found (%) | 70.69 | 10.51 | 6.58 | 8.19 |

Mass (m/Z): 426 (M+, $Cl^{37}$), 424 (M+, $Cl^{35}$)
NMR (δ, $CDCl_3$): 1.60 (9H, s), 1.68 (3H, s), 1.8–2.2 (12H), 2.14 (3H, d, J=2), 2.24 (9H, s), 2.3–2.5 (2H), 3.2–3.5 (2H), 5.08 (3H, m), 5.56 (1H, br, s), 6.04 (1H, br).

EXAMPLE 13

N-(3,7,11,15-Tetramethyl-2,6,10,14-hexadecatetraenoyl)-N',N',N'-trimethylethylenediamine iodide 3.4 g of methyl iodide was added to 6.5 g of N-(3,7,11,15-tetramethyl-2,6,10,14-hexadecatetraenoyl)-N',N'-dimethylethylenediamine obtained in Example 11. The mixture was left to stand at room temperature for 15 minutes. An excess amount of methyl iodide was distilled off to afford 9.0 g of the title compound as a brown solid with a melting point in the range of 53° to 55° C.

Elemental analysis for $C_{25}H_{45}N_2OI$

|  | C | H | N | I |
|---|---|---|---|---|
| calculated (%) | 58.17 | 8.78 | 5.42 | 24.57 |
| found (%) | 57.98 | 8.80 | 5.41 | 24.66 |

Mass (m/Z): 516 (M+)
NMR (δ, $CDCl_3$): 1.60 (9H, s), 1.68 (3H, s), 1.8–2.2 (12H), 2.16 (3H, d, J=2), 3.46 (9H, s), 3.84 (4H, br, s), 5.08 (3H, m), 5.72 (1H, br, s), 7.40 (1H, br).

EXAMPLE 14

N-Methyl-N-(3,7,11,15-tetramethyl-2,6,10,14-hexadecatetraenoyl)-ethanolamine

The procedure of Example 1 was repeated except that 6.1 g of 3,7,11,15-tetramethyl-2,6,10,14-hexadecatetraenoic acid and 2.4 ml of N-methylethanolamine were used. 6.6 g (yield 92%) of the title compound was obtained as a colorless oil.

Elemental analysis for $C_{23}H_{39}NO_2$

|  | C | H | N |
|---|---|---|---|
| calculated (%) | 76.40 | 10.87 | 3.87 |
| found (%) | 76.38 | 10.90 | 3.90 |

Mass (m/Z): 361 (M+)
NMR (δ, $CDCl_3$): 1.58 (9H, s), 1.64 (3H, s), 1.8–2.2 (12H), 2.12 (3H, s), 2.95 (3H, d, J=1), 3.2–3.8 (4H), 4.30 (1H, br), 5.06 (3H, m), 5.76 (1H, br, s).

EXAMPLE 15

N-(3,7,11,15-Tetramethyl-2,6,10,14-hexadecatetraenoyl)-3-hydroxypiperidine

The procedure of Example 1 was repeated except that 6.1 g of 3,7,11,15-tetramethyl-2,6,10,14-hexadecatetraenoic acid and 3.0 g of 3-hydroxypiperidine were used as starting materials. 7.4 g (yield 96%) of the title compound was obtained as a colorless oil.

Elemental analysis for $C_{25}H_{41}NO_2$

|  | C | H | N |
|---|---|---|---|
| calculated (%) | 77.47 | 10.67 | 3.61 |
| found (%) | 77.41 | 10.71 | 3.59 |

Mass (m/Z): 387 (M+)
NMR (δ, $CDCl_3$): 1.60 (9H, s), 1.68 (3H, s), 1.6–2.2 (16H), 2.12 (3H, br, s), 2.7–3.9 (6H), 5.08 (3H, m), 5.82 (1H, br, s).

EXAMPLE 16

N-(3,7,11,15-Tetramethyl-2,6,10,14-hexadecatetraenoyl)-2-hydroxymethylpiperidine The procedure of Example 1 was repeated except that 6.1 g of 3,7,11,15-tetramethyl-2,6,10,14-hexadecatetraenoic acid and 3.5 g of 2-hydroxymethylpiperidine were used as starting materials. 7.5 g (yield 94%) of the title compound was obtained as a colorless oil.

Elemental analysis for $C_{26}H_{43}NO_2$

|  | C | H | N |
|---|---|---|---|
| calculated (%) | 77.75 | 10.79 | 3.49 |
| found (%) | 77.73 | 10.83 | 3.30 |

Mass (m/Z): 401 (M+)
NMR (δ, $CDCl_3$): 1.60 (9H, s), 1.68 (3H, s), 1.7–2.2 (18H), 2.12 (3H, br, s), 3.2–4.0 (6H), 5.08 (3H, m), 5.74 (1H, br).

EXAMPLE 17

N-(3,7,11,15-Tetramethyl-2,6,10,14-hexadecatetraenoyl)-propanolamine

The procedure of Example 1 was repeated except that 6.1 g of 3,7,11,15-tetramethyl-2,6,10,14-hexadecatetraenoic acid and 2.3 ml of propanolamine were used as starting materials. 6.6 g (yield 92%) of the title compound was obtained as a colorless oil.

Elemental analysis for $C_{23}H_{39}NO_2$

|  | C | H | N |
|---|---|---|---|
| calculated (%) | 76.40 | 10.87 | 3.87 |
| found (%) | 76.23 | 10.95 | 3.77 |

Mass (m/Z): 361 (M+)
NMR (δ, $CDCl_3$): 1.59 (9H, s), 1.67 (3H, s), 1.5–1.8 (2H), 2.13 (3H, d, J=1), 1.9–2.2 (13H), 3.3–3.7 (4H), 5.09 (3H, m), 5.56 (1H, br, s), 6.03 (1H, t, J=6).

EXAMPLE 18

N-(3,7,11,15-Tetramethyl-2,6,10,14-hexadecatetraenoyl)-amyl alcoholamine

The procedure of Example 1 was repeated except that 6.1 g of 3,7,11,15-tetramethyl-2,6,10,14-hexadecatetraenoic acid and 3.1 g of amyl alcoholamine were used as starting materials. 7.4 g (yield 95%) of the title compound was obtained as a colorless oil.

Elemental analysis for $C_{25}H_{43}NO_2$

|  | C | H | N |
|---|---|---|---|
| calculated (%) | 77.07 | 11.13 | 3.60 |
| found (%) | 77.01 | 11.20 | 3.53 |

Mass (m/Z): 389 (M+)

NMR (δ, CDCl$_3$): 1.4–1.8 (6H, m), 1.60 (9H, s), 1.68 (3H, s), 1.9–2.2 (12H), 2.13 (3H, d, J=1), 2.44 (1H, s), 3.1–3.7 (4H), 5.10 (3H, m), 5.54 (1H, br, s), 5.71 (1H, t, J=5).

EXAMPLE 19

1-(3,7,11,15-Tetramethyl-2,6,10,14-hexadecatetraenoyl)-4-methylpiperazine

The procedure of Example 9 was repeated except that 6.1 g of 3,7,11,15-tetramethyl-2,6,10,14-hexadecatetraenoic acid and 3.3 ml of 1-methylpiperazine were used as starting materials. 6.9 g (yield 90%) of the title compound was obtained as a colorless oil.

Elemental analysis for $C_{25}H_{42}N_2O$

|  | C | H | N |
|---|---|---|---|
| calculated (%) | 77.66 | 10.95 | 7.25 |
| found (%) | 77.45 | 11.10 | 7.30 |

Mass (m/Z): 386 (M+)

NMR (δ, CDCl$_3$): 1.60 (9H, s), 1.68 (3H, s), 1.86 (3H, d, J=1), 1.9–2.2 (12H), 2.29 (3H, s), 2.2–2.45 (4H), 3.4–3.7 (4H), 5.10 (3H, m), 5.74 (1H, br, s).

EXAMPLE 20

1-(3,7,11,15-Tetramethyl-2,6,10,14-hexadecatetraenoyl)-4-methyl-hexahydro-1,4-diazepine The procedure of Example 9 was repeated except that 6.1 g of 3,7,11,15-tetramethyl-2,6,10,14-hexadecatetraenoic acid and 3.4 g of 4-methyl-1H-hexahydro-1,4-diazepine were used as starting materials. 7.5 g (yield 94%) of the title compound was obtained as a colorless oil.

Elemental analysis for $C_{26}H_{44}N_2O$

|  | C | H | N |
|---|---|---|---|
| calculated (%) | 77.94 | 11.07 | 6.99 |
| found (%) | 77.85 | 11.10 | 7.03 |

Mass (m/Z): 400 (M+)

NMR (δ, CDCl$_3$): 1.60 (9H, s), 1.68 (3H, s), 1.91 (3H, d, J=1), 1.7–2.3 (14H), 2.35 (3H, s), 2.45–2.7 (4H), 3.4–3.75 (4H), 5.08 (3H, m), 5.78 (1H, br, s).

EXAMPLE 21

N-(3,7,11,15-Tetramethyl-2,6,10,14-hexadecatetraenoyl)-ethanethiolamine

The procedure of Example 1 was repeated except that 6.1 g of 3,7,11,15-tetramethyl-2,6,10,14-hexadecatetraenoic acid and 2.3 g of ethanethiolamine were used as starting materials. 6.0 g (yield 83%) of the title compound was obtained as a colorless oil.

Elemental analysis for $C_{22}H_{37}NOS$

|  | C | H | N | S |
|---|---|---|---|---|
| calculated (%) | 72.67 | 10.26 | 3.85 | 8.82 |
| found (%) | 72.55 | 10.31 | 3.80 | 8.91 |

Mass (m/Z): 363 (M+)

NMR (δ, CDCl$_3$): 1.60 (9H, s), 1.69 (3H, s), 1.9–2.3 (13H), 2.15 (3H, s), 2.5–2.8 (2H), 3.3–3.6 (2H), 5.11 (3H, m), 5.57 (1H, br, s), 5.85 (1H, br).

EXAMPLE 22

3-(3,7,11,15-Tetramethyl-2,6,10,14-hexadecatetraenoylamino)-1-ethylpiperidine The procedure of Example 9 was repeated except that 6.1 g of 3,7,11,15-tetramethyl-2,6,10,14-hexadecatetraenoic acid and 3.8 g of 3-amino-1-ethylpiperidine were used as starting materials. 7.4 g (yield 90%) of the title compound was obtained as a pale yellow oil.

Elemental analysis for $C_{27}H_{46}N_2O$

|  | C | H | N |
|---|---|---|---|
| calculated (%) | 78.20 | 11.18 | 6.76 |
| found (%) | 78.41 | 11.21 | 6.70 |

Mass (m/Z): 414 (M+)

NMR (δ, CDCl$_3$): 1.04 (3H, t), 1.58 (12H, s), 1.66 (3H, s), 1.7–2.5 (22'H, m), 4.08 (1H, m), 5.08 (3H, m), 5.56 (1H, s), 6.04 (1H, br).

EXAMPLE 23

2-(3,7,11,15-Tetramethyl-2,6,10,14-hexadecatetraenoylaminomethyl)-1-ethylpyrrolidine The procedure of Example 9 was repeated except that 6.1 g of 3,7,11,15-tetramethyl-2,6,10,14-hexadecatetraenoic acid and 3.8 g of 2-aminomethyl-1-ethylpyrrolidine were used as starting materials. 7.8 g (yield 94%) of the title compound was obtained as a brown oil.

Elemental analysis for $C_{27}H_{46}N_2O$

|  | C | H | N |
|---|---|---|---|
| calculated (%) | 78.20 | 11.18 | 6.76 |
| found (%) | 78.39 | 11.20 | 6.74 |

Mass (m/Z): 414 (M+)

NMR (δ, CDCl$_3$): 1.40 (3H, t), 1.58 (9H, s), 1.64 (3'H, s), 1.8–2.2 (20H, m), 2.6–3.4 (3H, m), 3.60 (3H, m), 5.08 (3H, m), 5.70 (1H, s), 7.76 (1H, br).

EXAMPLE 24

2-(3',7',11',15'-Tetramethyl-2',6',10',14'-hexadecatetraenoylamino)-1-ethylpiperidine

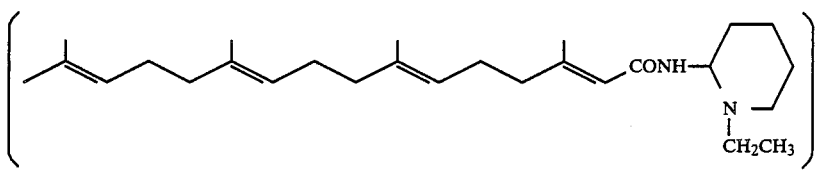

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added dropwise thereto under stirring and under cooling with ice. The mixture was stirred for 15 min.

2.8 g of 2-amino-1-ethylpiperidine was added thereto and the mixture was stirred at room temperature for 30 min and poured in ice-water. It was then extracted with ethyl acetate and washed with water. After drying over magnesium sulfate followed by distillation of the solvent, the resulting reaction mixture was treated by silica gel column chromatography to obtain 7.3 g (yield: 86%) of the title compound as a colorless oil.

Elemental analysis for $C_{27}H_{46}ON_2$

|  | C | H | N |
|---|---|---|---|
| calculated (%) | 78.20 | 11.18 | 6.76 |
| found (%) | 78.41 | 10.97 | 6.50 |

Mass (m/Z): 414 (M+)
NMR (δ, CDCl$_3$): 1.04 (3H, t, J=8), 1.59 (9H, S), 1.62 (3H, S), 1.9–2.6 (25H, m), 4.10 (1H, br, d), 5.08 (3H, br, t), 5.56 (1H, br, S), 6.10 (1H, br, d).

EXAMPLE 25

2-(3',7',11',15'-Tetramethyl-2',6',10',14'-hexadecatetraenoylaminomethyl)-1-ethylpyrrolidine

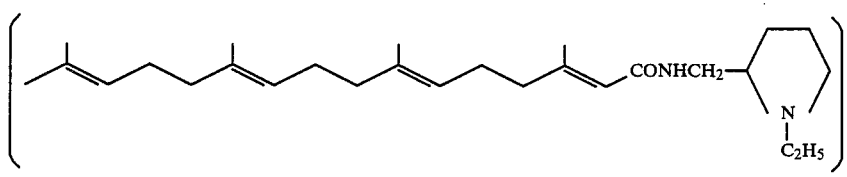

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added dropwise thereto under stirring and under cooling with ice. The mixture was stirred for 15 min.

2.8 g of 2-aminomethyl-1-ethylpyrrolidine was added thereto and the mixture was stirred at room temperature for 30 min and poured in ice-water. It was then extracted with ethyl acetate and washed with water. After drying over magnesium sulfate followed by concentration, the resulting concentrate was treated by silica gel column chromatography to obtain 7.5 g (91%) of the title compound.

Elemental analysis for $C_{27}H_{46}ON_2$

|  | C | H | N |
|---|---|---|---|
| calculated (%) | 78.20 | 11.18 | 6.76 |
| found (%) | 78.36 | 11.00 | 6.75 |

Mass (m/Z): 414 (M+)
NMR (δ, CDCl$_3$): 1.40 (3H, t, J=7), 1.60 (9H, S), 1.64 (3H, S), 1.8–2.3 (19H, m), 2.5–3.3 (4H, m), 3.4–3.8 (3H, m), 5.08 (5.68 (1H, br, S), 7.76 (1H, br).

EXAMPLE 26

N-(3,7,11,15-Tetramethyl-2,6,10,14-hexadecatetraenoylaminoethyl)-pyrrolidine

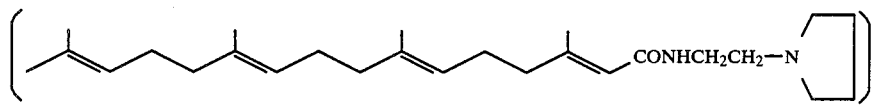

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added dropwise thereto under stirring and under cooling with ice and the mixture was stirred for 15 min.

2.3 g of 1-aminoethylpyrrolidine was added thereto and they were stirred at room temperature for 30 min and then poured in ice-water. It was then extracted with ethyl acetate and washed with water. After drying over magnesium sulfate followed by concentration, the resulting concentrate was treated by silica gel column chromatography to obtain 7.5 g (yield: 95%) of the title compound.

Elemental analysis for $C_{26}H_{44}ON_2$

|  | C | H | N |
|---|---|---|---|
| calculated (%) | 77.94 | 11.07 | 6.99 |
| found (%) | 77.72 | 11.13 | 6.87 |

Mass (m/Z): 400 (M+)
NMR (δ, CDCl$_3$): 1.60 (9H, S), 1.65 (3H, S), 1.8–2.2 (19H, m), 3.0–3.8 (8H, m), 4.76 (3H, m), 5.70 (1H, br, S), 7.50 (1H, br).

EXAMPLE 27

N-(3,7,11,15-Tetramethyl-2,6,10,14-hexadecatetra-enoylaminoethyl)-morpholine

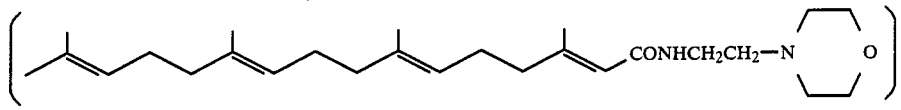

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added dropwise thereto under stirring and under cooling with ice and the mixture was stirred for 15 min.

2.6 g of 1-aminoethylmorpholine was added thereto and the mixture was stirred at room temperature for 30 min and then poured in ice-water. It was then extracted with ethyl acetate and washed with water. After drying over magnesium sulfate followed by concentration, the resulting concentrate was treated by silica gel column chromatography to obtain 7.6 g (91%) of the title compound.

Elemental analysis for $C_{26}H_{44}O_2N_2$

|  | C | H | N |
|---|---|---|---|
| calculated (%) | 74.95 | 10.65 | 6.72 |
| found (%) | 74.90 | 10.61 | 6.52 |

Mass (m/Z): 416 (M+)

NMR (δ, CDCl$_3$): 1.60 (9H, S), 1.68 (3H, S), 1.8–2.1 (15H, m), 2.4–2.6 (6H, m), 3.1–3.5 (2H, m), 3.6–3.8 (4H, m), 5.10 (3H, m), 5.54 (1H, br, S), 5.96 (1H, br).

EXAMPLE 28

N-(3,7,11,16-Tetramethyl-2,6,10,14-hexadecatetra-enoyl)-N',N'-dimethylethylenediamine hydrochloride

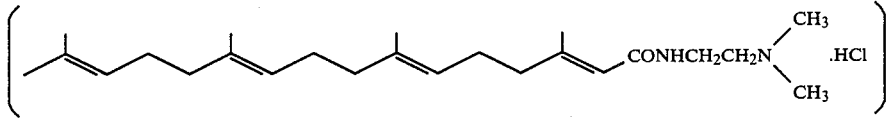

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added thereto under stirring and under cooling with ice and the mixture was stirred for 15 min.

1.7 g of N,N-dimethylethylenediamine was added therto and the mixture was stirred at room temperature for 30 min and then poured in ice-water. It was then extracted with ethyl acetate and washed with water. After drying over magnesium sulfate followed by concentration, the resulting concentrate was treated by silica gel column chromatography to obtain N-(3,7,11,15-tetramethyl-2,6,10,14-hexadecatetraenoyl-N',N'-dimethylethylenediamine. 20 ml of a 1.5M solution of hydrogen chloride in ethyl acetate was added thereto. After 1 h, the product was concentrated to obtain 7.4 g (90%) of the title compound.

Elemental analysis for $C_{24}H_{43}ON_2Cl$

|  | C | H | N | Cl |
|---|---|---|---|---|
| calculated (%) | 70.12 | 10.54 | 6.81 | 8.62 |
| found (%) | 70.01 | 10.60 | 6.95 | 8.77 |

NMR (δ, CDCl$_3$): 1.62 (9H, S), 1.68 (3H, S), 1.8–2.2 (16H, m), 2.92 (3H, S), 2.96 (3H, S), 3.2–3.8 (4H, m), 5.10 (3H, m), 5.76 (1H, br, S), 7.80 (1H, br, S).

EXAMPLE 29

N-(3,7,11,15-Tetramethyl-2,6,10,14-hexadecatetraen-oyl-N',N'-diethylethylenediamine

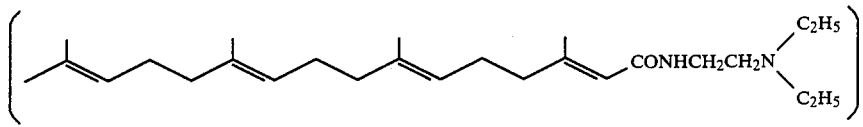

3.1 ml of triethylamine was added to a solution of 6.1 g of 3,7,11,15-tetramethyl-2,6,10,14-hexadecatetraenoic acid in tetrahydrofuran. 2.1 ml of ethyl chlorocarbonate was added dropwise thereto under stirring and under cooling with ice and the mixture was stirred for 15 min.

2.3 g of N,N-diethylethylenediamine was added thereto and the mixture was stirred at room temperature for 30 min and then poured in ice-water. It was then extracted with ethyl acetate and washed with water. After drying over mangesium sulfate followed by concentration, the resulting concentrate was treated by silica gel column chromatography to obtain 7.2 g (89%) of the title compound.

Elemental analysis for $C_{26}H_{46}ON_2$

|  | C | H | N |
|---|---|---|---|
| calculated (%) | 77.55 | 11.52 | 6.96 |
| found (%) | 77.43 | 11.63 | 7.01 |

Mass (m/Z): 402 (M+)

NMR (δ, CDCl$_3$): 1.02 (6H, t, J=8), 1.61 (9H, S), 1.68 (3H, S), 1.8–2.2 (15H, m), 2.3–2.7 (6H, m), 3.1–3.4 (2H, m), 5.10 (3H, m), 5.54 (1H, br, S), 6.04 (1H, br.).

EXAMPLE 30

N'-(3,7,11,15-Tetramethyl-2,6,10,14-hexadecatetraenoyl)-2-aminopyridine

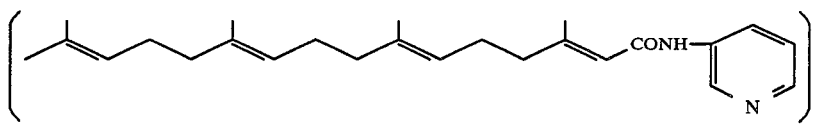

The same procedure as in Example 1 was repeated except that 6.1 g of 3,7,11,15-tetramethyl-2,6,10,14-hexadecatetraenoic acid and 1.9 g of 2-aminopyridine were used as the starting materials. 7.0 g (92%) of the title compound was obtained as a white wax.

Elemental analysis for $C_{25}H_{36}ON_2$

|  | C | H | N |
|---|---|---|---|
| calculated (%) | 78.90 | 9.54 | 7.36 |
| found (%) | 78.90 | 9.44 | 7.32 |

Mass (m/Z): 380 (M+)
NMR (δ, CDCl$_3$): 1.56 (9H, S), 1.65 (3H, S), 1.8–2.3 (15H, m), 5.05 (3H, m), 5.75 (1H, br, S), 7.20 (1H, br.), 8.1–8.6 (4H, m).

EXAMPLE 31

N-(3,7,11,15-Tetramethyl-2,6,10,14-hexadecatetraenoyl)-imidazole

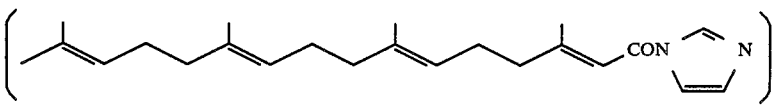

The same procedure as in Example 1 was repeated except that 6.1 g of 3,7,11,15-tetramethyl-2,6,10,14-hexadecatetraenoic acid and 1.4 g of imidazole were used as the starting materials. 6.5 g (91%) of the title compound was obtained as a colorless oil.

Elemental analysis for $C_{23}H_{34}ON_2$

|  | C | H | N |
|---|---|---|---|
| calculated (%) | 77.92 | 9.67 | 7.90 |
| found (%) | 77.85 | 9.71 | 7.92 |

Mass (m/Z): 354 (M+)
NMR (δ, CDCl$_3$): 1.57 (6H, S), 1.62 (3H, S), 1.66 (3H, S), 1.8–2.4 (15H, m), 5.08 (3H, m), 6.26 (1H, br, S), 7.04 (1H, br, S), 7.46 (1H, br, S), 8.12 (1H, S).

EXAMPLE 32

N-(3,7,11,15-Tetramethyl-2,6,10,14-hexadecatetraenoyl)-2-amino-2-ethyl-1,3-propanediol

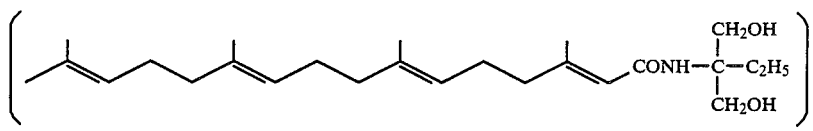

The same procedure as in Example 1 was repeated except that 6.1 g of 3,7,11,15-tetramethyl-2,6,10,14-hexadecatetraenoic acid and 2.4 g of 2-amino-1,3-propanediol were used as the starting materials. 7.5 g (92%) of the title compound was obtained as a colorless oil.

Elemental analysis for $C_{25}H_{43}O_3N$

|  | C | H | N |
|---|---|---|---|
| calculated (%) | 74.03 | 10.69 | 3.45 |
| found (%) | 73.94 | 10.82 | 3.40 |

Mass (m/Z): 405 (M+)
NMR (δ, CDCl$_3$): 0.90 (3H, t, J=8), 1.5–1.7 (14H, m), 1.8–2.2 (15H, m), 3.4–4.2 (6H, m), 5.08 (3H, m), 5.58 (1H, br. S), 5.72 (1H, br.).

EXAMPLE 33

N-(3,7,11,15-Tetramethyl-2,6,10,14-hexadecatetraenoyl)-3-amino-1,2-propanediol

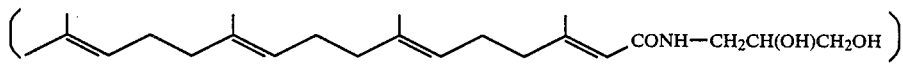

The same procedure as in Example 1 was repeated except that 6.1 g of 3,7,11,15-tetramethyl-2,6,10,14-hexadecatetraenoic acid and 1.9 g of 3-amino-1,2-propanediol were used as the starting materials. 6.5 g (86%) of the title compound was obtained as a white wax.

Elemental analysis for $C_{23}H_{39}O_3N$

|  | C | H | N |
|---|---|---|---|
| calculated (%) | 73.16 | 10.41 | 3.71 |
| found (%) | 73.08 | 10.45 | 3.65 |

Mass (m/Z): 377 (M+)

NMR (δ, CDCl$_3$): 1.60 (9H, S), 1.65 (3H, S), 1.8–2.2 (15H, m), 3.1–3.9 (7H, m), 5.07 (3H, m), 5.54 (1H, br. S), 5.84 (1H, br).

EXAMPLE 34

N-(3,7,11,15-Tetramethyl-2,6,10,14-hexadecatetraenoyl)-N',N',N'',N''-tetramethyldiethylenetriamine

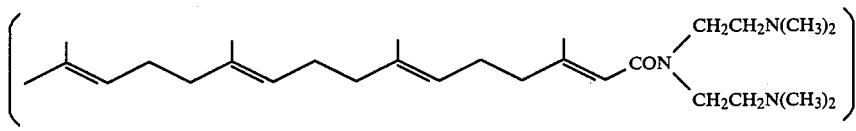

The same procedure as in Example 1 was repeated except that 6.1 g of 3,7,11,15-tetramethyl-2,6,10,14-hexadecatetraenoic acid and 3.2 g of N',N',N'',N''-tetramethyldiethylenetriamine were used as the starting materials. 8.0 g of the title compound was obtained as a colorless oil.

Elemental analysis for C$_{28}$H$_{51}$ON$_3$

|  | C | H | N |
|---|---|---|---|
| calculated (%) | 75.45 | 11.53 | 9.43 |
| found (%) | 75.10 | 11.50 | 9.38 |

Mass (m/Z): 445 (M+)

NMR (δ, CDCl$_3$): 1.60 (9H, S), 1.66 (3H, S), 1.8–2.2 (15H, m), 2.24 (12H, S), 2.3–2.6 (4H, m), 3.3–3.6 (4H, m), 5.08 (3H, m), 5.80 (1H, br.S).

EXAMPLE 35

N-(3,7,11,15-Tetramethyl-2,6,10,14-hexadecatetraenoyl)-N',N',N'',N''-tetramethyldiethylenetriamine dihydrochloride

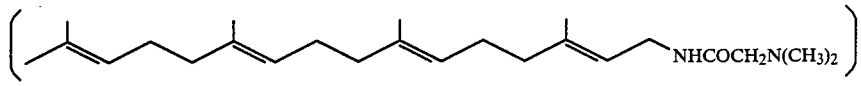

4.0 g of N-(3,7,11,15-tetramethyl-2,6,10,14-hexadecatetraenoyl)-N',N',N'',N''-tetramethyldiethylenetriamine obtained in Example 34 was treated with 20 ml of a 1.5M solution of hydrogen chloride in ethyl acetate at 5° C. for 30 min. The solvent was distilled off. After drying under reduced pressure, 4.6 g of the title compound was obtained as a brown wax.

Elemental analysis for C$_{28}$H$_{53}$ON$_3$Cl$_2$

|  | C | H | N | Cl |
|---|---|---|---|---|
| calculated (%) | 65.09 | 9.95 | 8.13 | 13.73 |
| found (%) | 64.94 | 9.90 | 8.20 | 13.91 |

NMR (δ, CDCl$_3$): 1.60 (9H, S), 1.67 (3H, S), 1.8–2.3 (15H, m), 2.92 (6H, S), 2.95 (6H, S), 3.1–4.1 (10H, m), 5.08 (3H, m), 6.06 (1H, br, S).

EXAMPLE 36

N-(3,7,11,15-Tetramethyl-2,6,10,14-hexadecatetraenyl)-N',N'-dimethylaminomethylcarboxamide

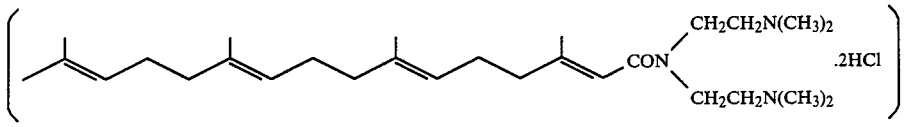

5.0 ml of triethylamine was added to a suspension of 5.0 g of N,N-dimethylglycine hydrochloride in dimethyl sulfoxide. 4.4 ml of ethyl chlorocarbonate was added dropwise thereto at 5° C. The mixture was stirred for 30 min.

11 g of 3,7,11,15-tetramethyl-2,6,10,14-hexadecatetraenylamine was added thereto and the mixture was stirred at room temperature for 2 h.

The reaction liquid was poured in ice-water. It was then extracted with chloroform and washed with water. After drying over magnesium sulfate followed by distillation of the solvent, the resulting reaction mixture was treated by silica gel chromatography to obtain 9.6 g (71%) of the title compound as a colorless oil.

Elemental analysis for C$_{24}$H$_{42}$ON$_2$

|  | C | H | N |
|---|---|---|---|
| calculated (%) | 76.95 | 11.30 | 7.48 |
| found (%) | 76.83 | 11.28 | 7.47 |

Mass (m/Z): 374 (M+)

NMR (δ, CDCl$_3$): 1.62 (9H, S), 1.70 (6H, S), 1.8–2.2 (12H, m), 2.28 (6H, S), 2.96 (2H, S), 3.96 (2H, t, J=6), 5.15 (4H, m), 7.05 (1H, br).

EXAMPLE 37

N-(3,7,11,14-Tetramethyl-2,6,10,14-hexadecatetraenyl)-2-aminoethylcarboxamide

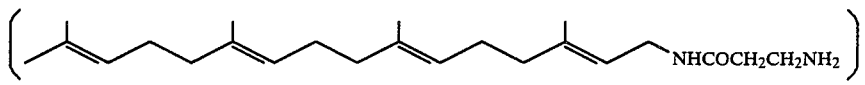

5.6 g of N-t-butyloxycarbonyl-β-alanine was dissolved in 40 ml of tetrahydrofuran. 4 ml of triethylamine was added thereto. 3.2 ml of ethyl chlorocarbonate was added dropwise thereto and the mixture was stirred for 30 min.

8.0 g of 3,7,11,15-tetramethyl-2,6,10,14-hexadecatetraenylamine was added thereto and the mixture was stirred at room temperature for 2 h.

The product was after-treated by an ordinary method. After a treatment by silica gel column chromatography, an N-t-butyloxycarbonyl derivative of the title compound was obtained. The product was dissolved in 100 ml of tetrahydrofuran. 30 ml of 5N hydrochloric acid solution was added thereto. After treatment at room temperature for 5 h followed by the treatment according to silica gel column chromatography, 7.2 g (50%) of the title compound was obtained as a colorless oil.

Elemental analysis for $C_{23}H_{40}ON_2$

|  | C | H | N |
|---|---|---|---|
| calculated (%) | 76.61 | 11.18 | 7.77 |
| found (%) | 76.56 | 11.23 | 7.70 |

Mass (m/Z): 360 (M+)

NMR (δ, CDCl₃): 1.60 (9H, S), 1.63 (6H, S), 1.8–2.4 (16H, m), 3.00 (2H, t, J=7), 3.82 (2H, t, J=6), 5.08 (4H, m), 6.78 (1H, br.).

EXAMPLE 38

N-(3,7,11,15-Tetramethyl-2,6,10,14-hexadecatetraenyl)-N',N'-dimethylethylenediamine

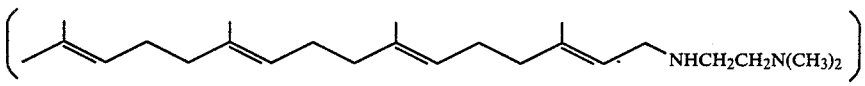

4.4 g of N,N-dimethylethylenediamine was dissolved in 40 ml of dioxane. 5 ml of pyridine was added to the solution. 17.6 g of 3,7,11,15-tetramethyl-2,6,10,14-hexadecatetraenyl bromide was added thereto and the mixture was heated under reflux for 2 h and poured in ice-water. After extraction with n-hexane followed by washing with water and concentration, the resulting reaction mixture was treated by alumina column chromatography to obtain 6 g (33%) of the title compound as a colorless oil.

Elemental analysis for $C_{24}H_{44}N_2$

|  | C | H | N |
|---|---|---|---|
| calculated (%) | 79.93 | 12.30 | 7.77 |
| found (%) | 79.90 | 12.31 | 7.83 |

Mass (m/Z): 360 (M+)

NMR (δ, CDCl₃): 1.52 (9H, S), 1.60 (3H, S), 1.63 (3H, S), 1.8–2.1 (12H, m), 2.12 (6H, S), 2.2–2.8 (5H, m), 3.07 (2H, br, d, J=8), 5.00 (4H, m).

EXAMPLE 39

N-[4-(2',6',10'-Trimethyl-1',5',9'-undecatrienyl)-benzoyl]ethanolamine

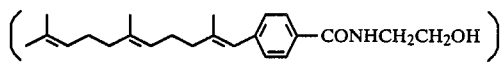

5 g of 4-(2',6',10'-trimethyl-1',5',9'-undecatrienyl)benzoic acid was dissolved in 30 ml of benzene. 2.3 g of thionyl chloride was added to the solution and the mixture was heated under reflux for 30 min and concentrated under reduced pressure.

The concentrate was dissolved in 30 ml of ether. 2 g of ethanolamine was added to the solution under cooling with ice and the mixture was stirred for 15 min. The reaction liquid was washed with 1N hydrochloric acid, then with aqueous sodium bicarbonate solution and finally with water. The liquid was dried over magnesium sulfate and concentrated. The concentrate was treated by alumina column chromatography to obtain 4.5 g (79%) of the title compound as a white crystal having a melting point of 43° to 44.5° C.

Elementary analysis for $C_{23}H_{33}O_2N$

|  | C | H | N |
|---|---|---|---|
| calculated (%) | 77.70 | 9.36 | 3.94 |
| found (%) | 77.82 | 9.45 | 3.89 |

Mass (m/Z): 355 (M+)

NMR (CDCl₃, δ): 1.58 (3H, S), 1.60 (3H, S), 1.63 (3H, S), 1.83 (3H, d, J=1), 1.9–2.3 (8H), 2.68 (1H, t, J=4), 3.5–3.9 (4H, m), 5.10 (2H, m), 6.24 (1H, S), 6.60 (1H, broad), 7.24 (2H, d, J=8), 7.50 (2H, d, J=8).

EXAMPLE 40

N-[4-(2',6',10'-Trimethyl-1',5',9'-undecatrienyl)-benzoyl]diethanolamine

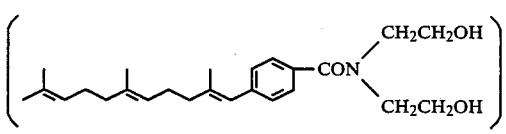

5 g of 4-(2',6',10'-trimethyl-1',5',9'-undecatrienyl)-benzoic acid and 3.4 g of diethanolamine were treated in the same manner as in Example 39 to obtain 5.4 g (85%) of the title compound as a colorless oil.

Elemental analysis for $C_{25}H_{37}O_3N$

|  | C | H | N |
|---|---|---|---|
| calculated (%) | 75.15 | 9.33 | 3.51 |
| found (%) | 75.09 | 9.42 | 3.49 |

Mass (m/Z): 399 (M+)
NMR (CDCl$_3$, δ): 1.57 (3H, S), 1.60 (3H, S), 1.64 (3H, S), 1.84 (3H, d J=2), 1.9–2.3 (8H), 3.4–4.0 (10H), 5.10 (2H, m), 6.21 (1H, S), 7.20 (2H, d J=8), 7.41 (2H, d J=8).

EXAMPLE 41

N-[4-(2′,6′,10′-Trimethyl-1′,5′,9′-undecatrienyl)-benzoyl]-N′,N′-dimethylethylenediamine

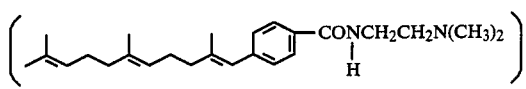

5 g of 4-(2′,6′,10′-trimethyl-1′,5′,9′-undecatrienyl)-benzoic acid and 2 g of N,N-dimethylethylenediamine were treated in the same manner as in Example 39 to obtain 5.3 g (86%) of the title compound as a colorless oil.

Elemental analysis for C$_{25}$H$_{38}$ON$_2$

|  | C | H | N |
|---|---|---|---|
| calculated (%) | 78.48 | 10.01 | 7.32 |
| found (%) | 78.53 | 10.13 | 7.36 |

Mass (m/Z): 382 (M+)
NMR (CDCl$_3$, δ): 1.58 (3H, S), 1.61 (3H, S), 1.65 (3H, S), 1.85 (3H, d J=2), 1.9–2.3 (8H), 2.24 (6H, S), 2.48 (2H, t J=5), 3.50 (2H, dt J=5.5) 5.10 (2H, m), 6.24 (1H, S), 6.75 (1H, t J=5), 7.24 (2H, d J=8), 7.70 (2H, d J=8).

EXAMPLE 42

N-[4-(2′,6′,10′-Trimethyl-1′,5′,9′-undecatrienyl)-benzoyl]-N′,N′-dimethylethylenediamine hydrochloride

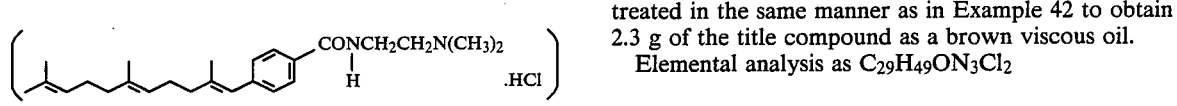

2 g of N-[4-(2′,6′,10′-trimethyl-1′,5′,9′-undecatrienyl)-benzoyl]-N′,N′-dimethylethylenediamine obtained in Example 41 was treated with 15 ml of a 1.5M solution of hydrogen chloride in ethyl acetate at 5° C. for 30 min. The solvent was distilled off. After drying under reduced pressure, 2.1 g of the title compound was obtained as a yellow, viscous oil.

Elemental analysis for C$_{25}$H$_{39}$ON$_2$Cl

|  | C | H | N | Cl |
|---|---|---|---|---|
| calculated (%) | 71.66 | 9.38 | 6.69 | 8.46 |
| found (%) | 71.39 | 9.49 | 6.47 | 8.52 |

NMR (CDCl$_3$, δ): 1.54 (3H, S), 1.56 (3H, S), 1.60 (3H, S), 1.80 (3H, S), 1.9–2.3 (8H), 2.85 (3H, S), 2.92 (3H, S), 3.34 (2H, m), 3.80 (2H, m), 5.10 (2H, m), 6.16 (1H, S), 7.18 (2H, d J=8), 7.90 (2H, d J=8), 8.60 (1H, br), 11.2 (1H, br).

EXAMPLE 43

N-[4-(2′,6′,10′-Trimethyl-1′,5′,9′-undecatrienyl)-benzoyl]-N′,N′,N″,N″-tetramethyldiethylenetriamine

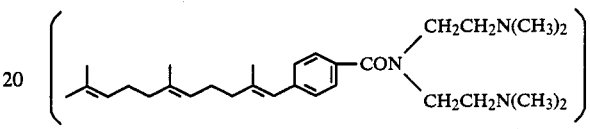

5 g of 4-(2′,6′,10′-trimethyl-1′,5′,9′-undecatrienyl)-benzoic acid and 3 g of N′,N′,N″,N″-tetramethyldiethylenetriamine were treated in the same manner as in Example 39 to obtain 6.6 g (91%) of the title compound as a colorless oil.

Elemental analysis as C$_{29}$H$_{47}$ON$_3$

|  | C | H | N |
|---|---|---|---|
| calculated (%) | 76.77 | 10.44 | 9.26 |
| found (%) | 76.73 | 10.49 | 9.38 |

Mass (m/Z): 453 (M+)
NMR (CDCl$_3$, δ): 1.58 (3H, S), 1.60 (3H, S), 1.64 (3H, S), 1.84 (3H, d J=2), 1.9–2.3 (8H), 2.24 (12H, S), 2.44 (4H, m), 3.40 (2H, t J=7), 3.48 (2H, t J=7), 5.10 (2H, m), 6.23 (1H, S), 7.21 (2H, d J=8), 7.45 (2H, d J=8).

EXAMPLE 44

N-[4-(2′,6′,10′-Trimethyl-1′,5′,9′-undecatrienyl)-benzoyl]-N′,N′,N″,N″-tetramethyldiethylenetriamine dihydrochloride

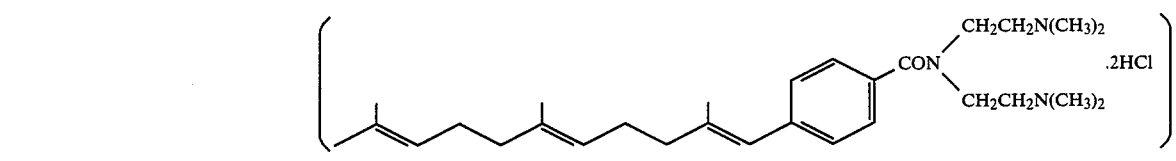

2 g of the compound obtained in Example 43 was treated in the same manner as in Example 42 to obtain 2.3 g of the title compound as a brown viscous oil.

Elemental analysis as C$_{29}$H$_{49}$ON$_3$Cl$_2$

|  | C | H | N | Cl |
|---|---|---|---|---|
| calculated (%) | 66.14 | 9.38 | 7.98 | 13.46 |
| found (%) | 65.88 | 9.51 | 7.76 | 13.38 |

NMR (CDCl$_3$, δ): 1.55 (3H, S), 1.57 (3H, S), 1.60 (3H, S), 1.83 (3H, S), 1.9–2.3 (8H), 2.83 (12H bS), 3.56 (4H, m), 4.00 (4H, m), 5.10 (2H, m), 6.20 (1H, S), 7.16 (2H, d J=8), 7.87 (2H, d J=8), 12.1 (2H, br).

EXAMPLE 45

N-[4-(2',6',10'-Trimethylundecyl)benzoyl]ethanolamine

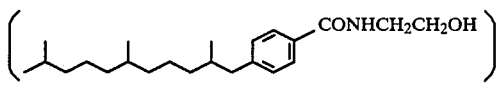

5 g of 4-(2',6',10'-trimethylundecyl)benzoic acid and 2 g of ethanolamine were treated in the same manner as in Example 39 to obtain 5.2 g (92%) of the title compound as a colorless oil.

Elemental analysis for $C_{23}H_{39}O_2N$

|  | C | H | N |
|---|---|---|---|
| calculated (%) | 76.40 | 10.87 | 3.87 |
| found (%) | 76.45 | 10.91 | 3.81 |

Mass (m/Z): 361 ($M^{30}$)
NMR (CDCl$_3$, δ): 0.80 (3H, d J32 7), 0.84 (9H, d J=7), 0.9–1.9 (15H), 2.35 (1H, dd J=12, 8), 2.65 (1H, dd J=12, 8), 2.76 (1H, bS), 3.5–3.9 (4H), 6.60 (1H, br), 7.16 (2H, d, J=8), 7.65 (2H, d, J=8).

EXAMPLE 46

N-[4-(2',6',10'-Trimethylundecyl)benzoyl]diethanolamine

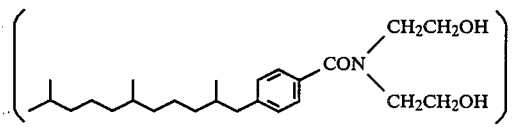

5 g of 4-(2',6',10'-trimethylundecyl)benzoic acid and 3.4 g of diethanolamine were treated in the same manner as in Example 39 to obtain 6.1 g (95%) of the title compound as a colorless oil.

Elemental analysis for $C_{25}H_{43}O_3N$

|  | C | H | N |
|---|---|---|---|
| calculated (%) | 74.03 | 10.69 | 3.45 |
| found (%) | 73.91 | 10.76 | 3.49 |

Mass (m/Z): 405 (M+)
NMR (CDCl$_3$, δ): 0.83 (3H, d, J=7), 0.87 (9H, d, J=7), 0.9–1.9 (15H), 2.33 (1H, dd, J=13, 8), 2.66 (1H, dd, J=13, 8), 3.4–4.0 (10H), 7.15 (2H, d, J=8), 7.39 (2H, d, J=8).

EXAMPLE 47

N-[4-(2',6',10'-Trimethylundecyl)benzoyl]-N',N'-dimethylethylenediamine

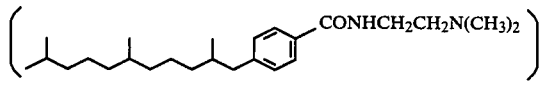

5 g of 4-(2',6',10'-trimethylundecyl)benzoic acid and 2 g of N,N-dimethylethylenediamine were treated in the same manner as in Example 39 to obtain 5.4 g (88%) of the title compound as a colorless oil.

Elemental analysis for $C_{25}H_{44}ON_2$

|  | C | H | N |
|---|---|---|---|
| calculated (%) | 77.26 | 11.41 | 7.21 |
| found (%) | 77.08 | 11.49 | 7.14 |

Mass (m/Z): 388 (M+)
NMR (CDCl$_3$, δ): 0.82 (3H, d, J=7), 0.85 (9H, d, J=7), 0.9–1.8 (15H), 2.24 (6H, S), 2.3–2.8 (4H, m), 3.49 (2H, dt, J=5, 5) 6.75 (1H, t, J=5), 7.16 (2H, d, J=7), 7.68 (2H, d, J=7).

EXAMPLE 48

N-[4-(2',6',10'-Trimethylundecyl)benzoyl]-N',N'-dimethylethylenediamine hydrochloride

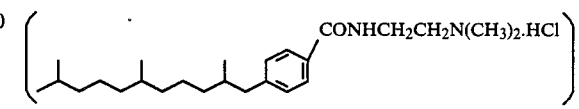

2 g of the compound obtained in Example 47 was treated in the same manner as in Example 42 to obtain 2.1 g of the title compound as a colorless, viscous liquid.

Elemental analysis for $C_{25}H_{45}ON_2Cl$

|  | C | H | N | Cl |
|---|---|---|---|---|
| calculated (%) | 70.64 | 10.67 | 6.59 | 8.34 |
| found (%) | 70.45 | 10.79 | 6.53 | 8.28 |

NMR (CDCl$_3$, δ): 0.78 (3H, d, J=7), 0.83 (9H, d, J=7), 0.9–1.8 (15H), 2.2–2.8 (2H, m), 2.88 (3H, S), 2.92 (3H, S), 3.2–3.9 (4H), 7.12 (2H, d, J=7), 7.88 (2H, d, J=7), 8.58 (1H, t, J=5), 11.8 (1H, br).

EXAMPLE 49

N-[4-(2',6',10'-Trimethylundecyl)benzoyl]-N',N',N'',N''-tetramethyldiethylenetriamine

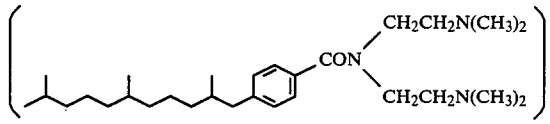

5 g of 4-(2',6',10'-trimethylundecyl)benzoic acid and 3 g of N',N',N'',N''-tetramethyldiethylenetriamine were treated in the same manner as in Example 39 to obtain 6.4 g (89%) of the title compound as a colorless oil.

Elemental analysis for $C_{29}H_{53}ON_3$

|  | C | H | N |
|---|---|---|---|
| calculated (%) | 75.76 | 11.62 | 9.14 |
| found (%) | 75.63 | 11.68 | 9.09 |

Mass (m/Z): 459 (M+)
NMR (CDCl$_3$, δ): 0.81 (3H, d, J=7), 0.85 (9H, d, J=7), 0,9–1.8 (15H), 2.25 (12H, S), 2.3–2.8 (6H, m), 3.41 (2H, t, J=7), 3.49 (2H, t, J=7), 7.13 (2H, d, J=7), 7.44 (2H, d, J=7).

EXAMPLE 50

N-[4-(2',6',10'-Trimethylundecyl)benzoyl]-N',N',N'',N''-tetramethyldiethylenetriamine dihydrochloride

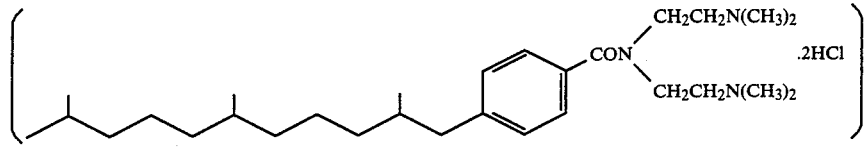

2 g of the compound obtained in Example 49 was treated in the same manner as in Example 42 to obtain 2.3 g of the title compound as a brown wax.
Elemental analysis for $C_{29}H_{55}ON_3Cl_2$

|  | C | H | N | Cl |
|---|---|---|---|---|
| calculated (%) | 65.39 | 10.41 | 7.89 | 13.31 |
| found (%) | 65.18 | 10.50 | 7.77 | 13.29 |

NMR (CDCl$_3$, δ): 0.79 (3H, d, J=7), 0.85 (9H, d, J=7), 0.9-1.8 (15H), 2.1-2.8 (2H), 2.84 (12H, bS), 3.58 (4H, m), 4.00 (4H, m), 6.72 (2H, bS), 7.16 (2H, d, J=7), 7.48 (2H, d, J=7).

EXAMPLE 51

N-[4-(2',6'-Dimethylheptyl)benzoyl]ethanolamine

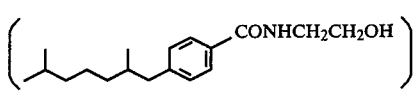

5 g of 4-(2',6'-dimethylheptyl)benzoic acid and 3 g of ethanolamine used as starting materials were treated in the same manner as in Example 39 to obtain 5.1 g (85% of the title compound as white crystals.
Melting point (°C.): 72.5 to 73.5.
Elemental analysis for $C_{18}H_{29}O_2N$

|  | C | H | N |
|---|---|---|---|
| calculated (%) | 74.18 | 10.03 | 4.81 |
| found (%) | 74.24 | 10.09 | 4.77 |

Mass (m/Z): 291 (M+)
NMR (CDCl$_3$, δ): 0.81 (3H, d, J=7), 0.86 (6H, d, J=7), 0.9-1.8 (8H), 2.36 (1H, dd, J=13, 8), 2.66 (1H, dd, J=13, 8), 2.85 (1H, br), 3.4-3.9 (4H, m), 6.76 (1H, br), 7.16 (2H, d, J=8), 7.66 (2H, d, J=8).

EXAMPLE 52

N-[4-(2',6'-Dimethylheptyl)benzoyl]-N',N',N'',N''-tetramethyldiethylenetriamine

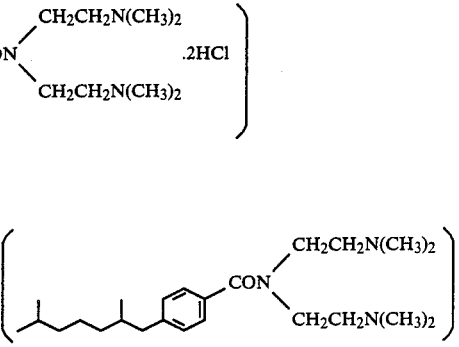

5 g of 4-(2',6'-dimethylheptyl)benzoic acid and 4.5 g of N',N',N'',N''-tetramethyldiethylenetriamine were treated in the same manner as in Example 39 to obtain 6.6 g (84%) of the title compound as a colorless oil.
Elemental analysis for $C_{24}H_{43}ON_3$

|  | C | H | N |
|---|---|---|---|
| calculated (%) | 73.98 | 11.12 | 10.79 |
| found (%) | 73.85 | 11.18 | 10.66 |

Mass (m/Z): 389 (M+)
NMR (CDCl$_3$, δ): 0.82 (3H, d, J=7), 0.85 (6H, d, J=7), 0.9-1.8 (8H), 2.15 (12H, bS), 2.2-2.7 (6H, m), 3.44 (4H, b), 7.09 (2H, d, J=8), 7.25 (2H, d, J=8).

EXAMPLE 53

N-[4-(2',6',10',14'-Tetramethylpentadecyl)benzoyl]ethanolamine

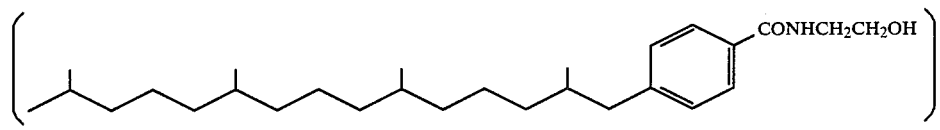

5 g of 4-(2',6',10',14'-tetramethylpentadecyl)benzoic acid and 2 g of ethanolamine were treated in the same manner as in Example 39 to obtain 5.0 g (90%) of the title compound as a colorless oil.
Elemental analysis for $C_{28}H_{49}O_2N$

|  | C | H | N |
|---|---|---|---|
| calculated (%) | 77.90 | 11.44 | 3.24 |
| found (%) | 77.72 | 11.56 | 3.31 |

Mass (m/Z): 431 (M+)
NMR (CDCl$_3$, δ): 0.80 (3H, d, J=7), 0.85 (12H, d, J=7), 0.9-1.8 (22H), 2.32 (1H, dd J=12, 8), 2.65 (1H, dd J=12, 8), 3.4÷3.9 (5H, m), 6.78 (1H, b), 7.12 (2H, d, J=8), 7.65 (2H, d, J=8).

EXAMPLE 54

N-[4-(2',6',10',14'-Tetramethylpentadecyl)benzoyl]N',-N',N'',N'''-tetramethyldiethylenetriamine

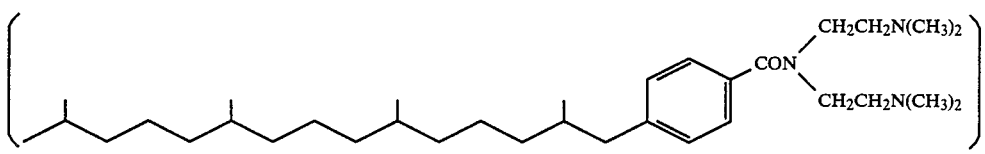

5 g of 4-(2',6',10',14'-tetramethylpentadecyl)benzoic acid and 3 g of N',N',N'',N'''-tetramethyldiethylenetriamine were treated in the same manner as in Example 39 to obtain 6.2 g (91%) of the title compound as a colorless oil.

Elemental analysis for $C_{34}H_{63}ON_3$

|  | C | H | N |
|---|---|---|---|
| calculated (%) | 77.06 | 11.98 | 7.93 |
| found (%) | 76.92 | 12.04 | 7.88 |

Mass (m/Z): 529 (M+)

NMR (CDCl$_3$, δ): 0.80 (3H, d, J=7), 0.84 (12H, d, J=7), 0.9-1.8 (22H), 2.18 (12H, bS), 2.2-2.7 (6H, m), 3.44 (4H, b), 7.10 (2H, d, J=8), 7.25 (2H, d, J=8).

EXAMPLE 55

N-{3-[4'-(4'',8''-Dimethylnonyl)phenyl]butanoyl}-ethanolamine

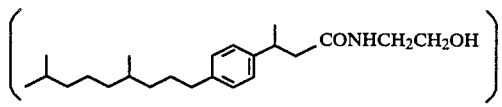

5 g of 3-[4'-(4'',8''-dimethylnonyl)phenyl]butanoic acid and 2 g of ethanolamine were treated in the same manner as in Example 39 to obtain 4.5 g (80%) of the title compound.

Elemental analysis for $C_{23}H_{39}O_2N$

|  | C | H | N |
|---|---|---|---|
| calculated (%) | 76.40 | 10.87 | 3.87 |
| found (%) | 76.51 | 11.03 | 3.85 |

Mass (m/Z): 361 (M+)

NMR (CDCl$_3$, δ): 0.84 (9H, d, J=7), 1.30 (3H, d, J=7), 0.9-1.8 (12H), 2.1-2.6 (5H, m), 3.1-3.6 (5H, m), 5.83 (1H, b), 7.10 (4H, S).

EXAMPLE 56

N-{3-[4'-(4'',8''-Dimethylnonyl)phenyl]butanoyl}-N',N',N'',N'''-tetramethyldiethylenetriamine

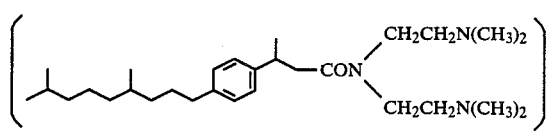

5 g of 3-[4'-(4'',8''-dimethylnonyl)phenyl]butanoic acid was dissolved in 30 ml of benzene. 2.3 g of thionyl chloride was added to the solution. The mixture was heated under reflux for 30 min and then concentrated under reduced pressure.

The concentrate was dissolved in 30 ml of ether. 3 g of N',N',N'',N'''-tetramethyldiethylenetriamine was added to the solution under cooling with ice and the mixture was stirred for 15 min.

The reaction liquid was washed with 1N hydrochloric acid and then with water, dried over magnesium sulfate and concentrated. The concentrate was treated by column chromatography to obtain 6.1 g (85%) of the title compound as a colorless oil.

Elemental analysis for $C_{24}H_{53}ON_3$

|  | C | H | N |
|---|---|---|---|
| calculated (%) | 75.76 | 11.62 | 9.14 |
| found (%) | 75.59 | 11.81 | 9.05 |

Mass (m/Z): 459 (M+)

NMR (CDCl$_3$, δ): 0.84 (9H, d, J=7), 1.28 (3H, d, J=7), 0.9-1.8 (12H), 2.10 (6H, S), 2.12 (6H, S), 2.2-2.6 (9H), 3.1-3.5 (4H, m), 7.08 (4H, S).

EXAMPLE 57

N-{3-[4'-(4'',8''-Dimethylnonyl)phenyl]-2-butenoyl}-ethanolamine

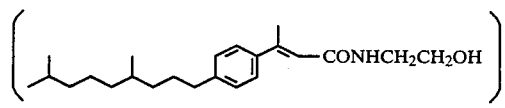

5 g of 3-[4'-(4'',8''-dimethylnonyl)phenyl]-2-butenoic acid and 2 g of ethanolamine were treated in the same manner as in Example 39 to obtain 4.4 g (78%) of the title compound as white crystals.

Melting point (°C.): 48.0 to 49.5.

Elemental analysis for $C_{23}H_{37}O_2N$

|  | C | H | N |
|---|---|---|---|
| calculated (%) | 76.83 | 10.37 | 3.90 |
| found (%) | 76.71 | 10.52 | 3.86 |

Mass (m/Z): 359 (M+)

NMR (CDCl$_3$, δ): 0.84 (9H, d, J=7), 0.9-1.8 (12H), 2.50 (3H, d, J=1), 2.4-2.7 (2H, m), 3.3-3.8 (5H, m), 6.02 (1H, q, J=1), 6.38 (1H, t, J=5), 7.09 (2H, d, J=9), 7.30 (2H, d, J=9).

EXAMPLE 58

N-{3-[4'-(4″,8″-Dimethylnonyl]-2-butenoyl}-N',N',N″,N‴-tetramethyldiethylenetriamine

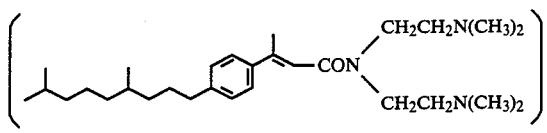

5 g of 3-[4'-(4″,8″-dimethylnonyl)phenyl]-2-butenoic acid was dissolved in 30 ml of benzene. 5 g of 3-[4'-(4″,8″-dimethylnonyl)phenyl]-2-butenoic acid and 3 g of N',N',N″,N‴-tetramethyldiethylenetriamine were treated in the same manner as in Example 39 to obtain 5.4 g (75%) of the title compound as a colorless oil.

Elemental analysis of $C_{29}H_{51}ON_3$

|  | C | H | N |
|---|---|---|---|
| calculated (%) | 76.09 | 11.23 | 9.18 |
| found (%) | 75.88 | 11.39 | 9.15 |

Mass (m/Z): 457 (M+)

NMR (CDCl$_3$, δ): 0.85 (9H, d, J=6), 0.9–1.8 (12H), 2.22 (6H, S), 2.28 (9H, S), 2.3–2.7 (6H), 3.3–3.6 (4H, m), 6.30 (1H, q, J=1), 7.13 (2H, d, J=8), 7.34 (2H, d, J=8).

EXAMPLE 59

N-[2-Methyl-4-(2',6',10'-trimethylundecyl)benzoyl]ethanolamine

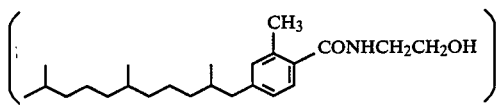

3 g of 2-methyl-4-(2',6',10'-trimethylundecyl)benzoic acid and 1.5 g of ethanolamine were treated in the same manner as in Example 39 to obtain 2.9 g (86%) of the title compound as white crystals.

Melting point (°C.): 48.5 to 49.5.
Elemental analysis for $C_{24}H_{41}O_2N$

|  | C | H | N |
|---|---|---|---|
| calculated (%) | 76.75 | 11.00 | 3.73 |
| found (%) | 76.58 | 11.19 | 3.76 |

Mass (m/Z): 375 (M+)

NMR (CDCl$_3$, δ): 0.80 (3H, d, J=7), 0.84 (9H, d, J=7), 0.9–1.8 (15H), 2.25 (1H, dd, J=12, 8), 2.60 (1H, dd, J=12, 8), 2.40 (3H, S), 2.90 (1H, b), 3.4–3.9 (4H, m), 6.31 (1H, b), 6.8–7.3 (3H, m).

EXAMPLE 60

N-[2-Methyl-4-(2',6',10'-trimethylundecyl)benzoyl]-N',N',N″,N‴-tetramethyldiethylenetriamine

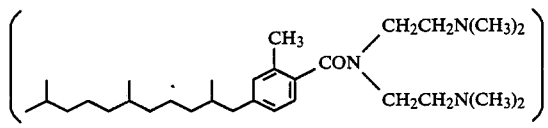

3 g of 2-methyl-4-(2',6',10'-trimethylundecyl)benzoic acid and 2 g of N',N',N″,N‴-tetramethyldiethylenetriamine were treated in the same manner as in Example 39 to obtain 3.4 g (79%) of the title compound as a colorless oil.

Elemental analysis for $C_{30}H_{55}ON_3$

|  | C | H | N |
|---|---|---|---|
| calculated (%) | 76.05 | 11.70 | 8.87 |
| found (%) | 75.89 | 11.90 | 8.92 |

Mass (m/Z): 473 (M+)

NMR (CDCl$_3$, δ): 0.81 (3H, d, J=8), 0.85 (9H, d, J=7), 0.9–1.8 (15H), 1.96 (6H, S), 2.24 (3H, S), 2.28 (6H, S), 2.1–2.7 (6H, m), 3.1–3.7 (4H, m), 6.8–7.1 (3H, m).

EXAMPLE 61

N-[2-(Fluoro-4-(2',6',10'-trimethylundecyl)benzoyl]ethanolamine

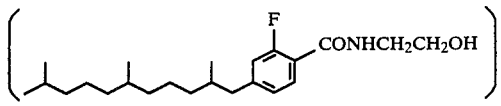

3 g of 2-fluoro-4-(2',6',10'-trimethylundecyl)benzoic acid and 1.5 g of ethanolamine were treated in the same manner as in Example 39 to obtain 2.9 g (87%) of the title compound as a colorless oil.

Elemental analysis for $C_{23}H_{38}O_2NF$

|  | C | H | N | F |
|---|---|---|---|---|
| calculated (%) | 72.79 | 10.09 | 3.69 | 5.01 |
| found (%) | 72.58 | 10.15 | 3.67 | 5.13 |

Mass (m/Z): 379 (M+)

NMR (CDCl$_3$, δ): 0.78 (3H, d J=7), 0.84 (9H, d J=7), 0.9–1.8 (15H), 2.46 (1H, dd, J=14, 8), 2.80 (1H, dd, J=14, 8), 3.15 (1H, br), 3.3–3.8 (4H, m), 6.44 (1H, t, J=5), 6.7–7.3 (3H, m).

EXAMPLE 62

N-[2-Chloro-4-(2',6',10'-trimethylundecyl)benzoyl]-N',N',N″,N‴-tetramethyldiethylenetriamine

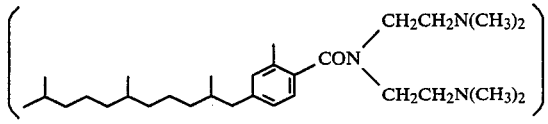

2.5 g of 2-chloro-4-(2',6',10'-trimethylundecyl)benzoic acid and 1.5 g of N',N',N″,N‴-tetramethyldiethylenetriamine were treated in the same manner as in Example 39 to obtain 3.2 g (91%) of the title compound as a colorless oil.

Elemental analysis for $C_{29}H_{52}ON_3F$

|  | C | H | N | F |
|---|---|---|---|---|
| calculated (%) | 72.91 | 10.97 | 8.80 | 3.98 |
| found (%) | 72.75 | 10.91 | 8.93 | 3.95 |

Mass (m/Z): 477 (M+)

NMR (CDCl$_3$, δ): 0.83 (3H, d, J=7), 0.85 (9H, d, J=7), 0.9-1.7 (15H), 2.04 (6H, S), 2.28 (6H, S), 2.1-2.7 (6H, m), 3.16 (4H, t, J=7), 6.8-7.2 (3H, m).

EXAMPLE 63

N-[4-(2′,6′,10′-Trimethylundecyl)-1-naphthoyl]ethanolamine

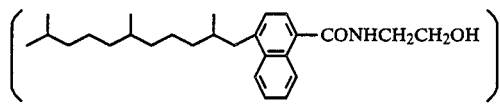

5 g of 4-(2′,6′,10′-trimethylundecyl)-1-naphthoic acid and 2 g of ethanolamine were treated in the same manner as in Example 39 to obtain 5.2 g (93%) of the title compound as white crystals.

Melting point (°C.): 61 to 62.

Elemental analysis for C$_{27}$H$_{41}$O$_2$N

|  | C | H | N |
| --- | --- | --- | --- |
| calculated (%) | 78.78 | 10.04 | 3.40 |
| found (%) | 78.85 | 10.13 | 3.51 |

Mass (m/Z): 411 (M+)

NMR (CDCl$_3$, δ): 0.80 (12H, d, J=7), 0.9-1.9 (16H), 2.66 (1H, dd, J=14, 8), 3.09 (1H, dd, J=14, 8), 3.4-3.8 (4H, m), 6.56 (1H, t, J=5), 7.0-8.3 (6H, m).

EXAMPLE 64

N-[4-(2′,6′,10′-Trimethylundecyl)-1-naphthoyl]-N′,N′,N″,N″-tetramethyldiethylenetriamine

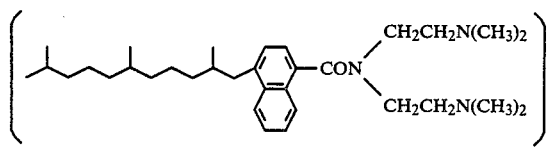

5 g of 4-(2′,6′,10′-trimethylundecyl)-1-naphthoic acid and 3 g of N′,N′,N″,N″-tetramethyldiethylenetriamine were treated in the same manner as in Example 39 to obtain 6.1 g (88%) of the title compound as a colorless oil.

Elemental analysis for C$_{33}$H$_{55}$ON$_3$

|  | C | H | N |
| --- | --- | --- | --- |
| calculated (%) | 77.74 | 10.88 | 8.24 |
| found (%) | 77.58 | 10.95 | 8.24 |

Mass (m/Z): 509 (M+)

NMR (CDCl$_3$, δ): 0.84 (12H, d, J=7), 0.9-1.7 (15H), 1.86 (6H, S), 2.0-2.3 (2H, m), 2.36 (6H, S), 2.5-3.3 (8H, m), 7.2-8.1 (6H, m).

EXAMPLE 65

N-[5-(2′,6′,10′-Trimethylundecyl)-1-naphthoyl]ethanolamine

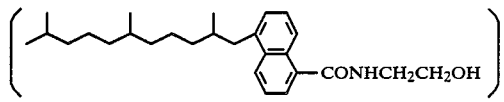

5 g of 5-(2′,6′,10′-trimethylundecyl)-1-naphthoic acid and 2 g of ethanolamine were treated in the same manner as in Example 39 to obtain 5.2 g (93%) of the title compound as a colorless oil.

Elemental analysis for C$_{27}$H$_{41}$O$_2$N

|  | C | H | N |
| --- | --- | --- | --- |
| calculated (%) | 78.78 | 10.04 | 3.40 |
| found (%) | 78.71 | 10.12 | 3.45 |

Mass (m/Z): 411 (M+)

NMR (CDCl$_3$, δ): 0.85 (12H, d, J=7), 0.9-2.0 (16H), 2.70 (1H, dd J=14, 6), 3.10 (1H, dd J=14, 6), 3.5-3.9 (4H, m), 6.47 (1H, t, J=5), 7.2-8.2 (6H, m).

EXAMPLE 66

N-[5-(2′,6′,10′-Trimethylundecyl)-1-naphthoyl]-N′,N′,N″,N″-tetramethyldiethylenetriamine

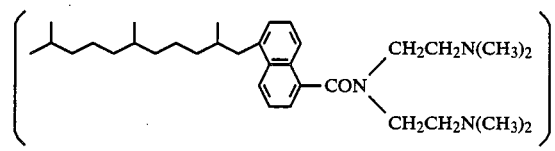

5 g of 5-(2′,6′,10′-trimethylundecyl)-1-naphthoic acid and 3 g of N′,N′,N″,N″-tetramethyldiethylenetriamine were treated in the same manner as in Example 39 to obtain 6.0 g (87%) of the title compound as a colorless oil.

Elemental analysis for C$_{33}$H$_{55}$ON$_3$

|  | C | H | N |
| --- | --- | --- | --- |
| calculated (%) | 77.74 | 10.88 | 8.24 |
| found (%) | 77.72 | 10.81 | 8.29 |

Mass (m/Z): 509 (M+)

NMR (CDCl$_3$, δ): 0.84 (12H, d, J=7), 0.9-1.8 (15H), 1.88 (6H, S), 2.1-2.3 (2H, m), 2.28 (6H, S), 2.5-3.3 (8H, m), 7.2-8.1 (6H, m).

EXAMPLE 67

N-[4-(2′,6′,10′-Trimethylundecyl)-5,6,7,8-tetrahydro-1-naphthoyl]ethanolamine

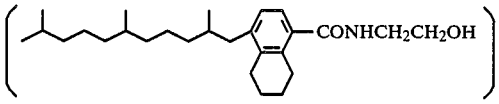

5 g of 4-(2′,6′,10′-trimethylundecyl)-5,6,7,8-tetrahydro-1-naphthoic acid and 2 g of ethanolamine were treated in the same manner as in Example 39 to obtain 5.2 g (92%) of the title compound as white crystals.
Melting point (°C.): 47–48.
Elemental analysis for $C_{27}H_{45}O_2N$

|  | C | H | N |
|---|---|---|---|
| calculated (%) | 78.02 | 10.91 | 3.37 |
| found (%) | 78.16 | 10.83 | 3.38 |

Mass (m/Z): 415 (M+)
NMR (CDCl$_3$, δ): 0.84 (3H, d, J=7), 0.85 (9H, d, J=7), 0.9–1.9 (19H), 2.23 (1H, dd, J=14, 8), 2.4–3.9 (5H, m), 3.10 (1H, br), 3.3–3.8 (4H, m), 6.30 (1H, t, J=5), 6.85 (1H, d, J=8), 7.04 (1H, d, J=8).

EXAMPLE 68

N-[4-(2',6',10'-Trimethylundecyl)-5,6,7,8-tetrahydro-1-naphthoyl]-N',N',N'',N''-tetramethyldiethylenetriamine

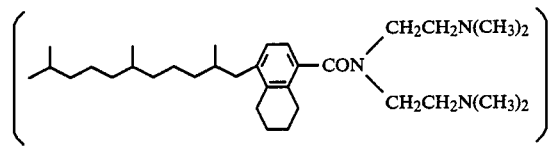

5 g of 4-(2',6',10'-trimethylundecyl)-5,6,7,8-tetrahydro-1-naphthoic acid and 3 g of N',N',N'',N''-tetramethyldiethylenetriamine were treated in the same manner as in Example 39 to obtain 5.7 g (82%) of the title compound as a colorless oil.
Elemental analysis for $C_{33}H_{59}ON_3$

|  | C | H | N |
|---|---|---|---|
| calculated (%) | 77.13 | 11.57 | 8.18 |
| found (%) | 77.20 | 11.54 | 8.25 |

Mass (m/Z): 513 (M+)
NMR (CDCl$_3$, δ): 0.82 (3H, d, J=7), 0.85 (9H, d, J=7), 0.9–1.9 (19H), 2.01 (6H, S), 2.30 (6H, S), 2.1–3.3 (14H), 6.88 (2H, S).

The embodiments of the invention in which an exclusive property of privilege is claimed are defined as follows:

1. A compound having the formula:

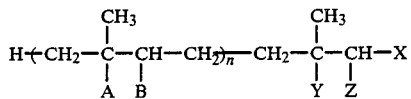

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; and X is selected from the group consisting of:

(1) a group of the formula

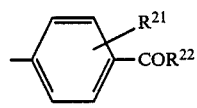

wherein $R^{22}$ is a group of the formula

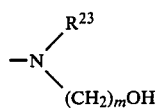

wherein $R^{23}$ is hydrogen or lower alkyl and m is an integer of from 1 to 5,
a group of the formula

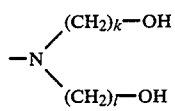

wherein k and l are the same or different and each is an integer of from 1 to 5,
a group of the formula

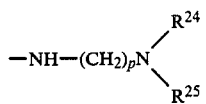

wherein p is an integer of from 0 to 5 and $R^{24}$ and $R^{25}$ are each hydrogen or lower alkyl,
or a group of the formula

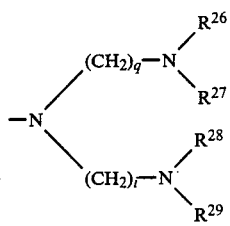

wherein q and i are each an integer of 1 to 5 and $R^{26}$, $R^{27}$, $R^{28}$ and $R^{29}$ are each a lower alkyl, and $R^{21}$ is hydrogen, a lower alkyl or a halogen atom, (2) a group of the formula

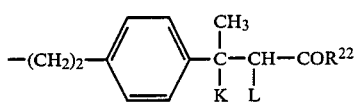

wherein K and L are both hydrogen or represent a direct valence bond between the carbon atoms to which they are attached and $R^{22}$ has the same meaning as defined above, (3) a group of the formula

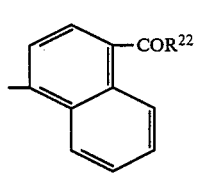

wherein $R^{22}$ has the same meaning as defined above, (4) a group of the formula

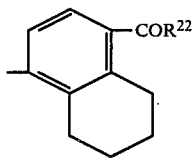

wherein $R^{22}$ has the same meaning as defined above, (5) a group of the formula

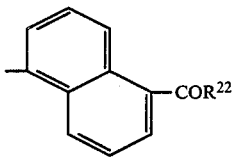

wherein $R^{22}$ has the same meaining as defined above, (6) a group of the formula

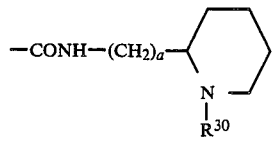

wherein a is zero or an integer of 1 to 5, and $R^{30}$ is a lower alkyl, (7) a group of the formula

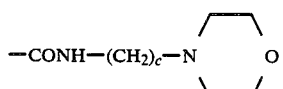

wherein c is zero or an integer of 1 to 5, (8) a group of the formula

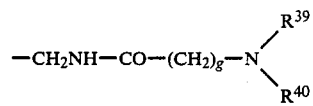

wherein g is an integer of 1 to 5 and $R^{39}$ and $R^{40}$ are each hydrogen or a lower alkyl, and (9) a group of the formula

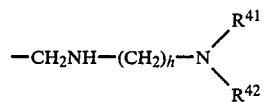

wherein h is an integer of 1 to 5 and $R^{41}$ and $R^{42}$ are each hydrogen or a lower alkyl,
or a pharmaceutically acceptable salt thereof.

2. A compound having the formula:

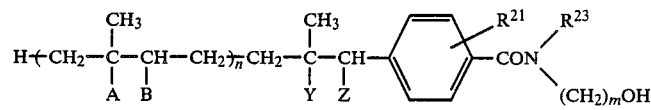

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; $R^{21}$ is hydrogen, a lower alkyl or a halogen; $R^{23}$ is hydrogen or lower alkyl and m is an integer from 1 to 5, or a pharmaceutically acceptable salt thereof.

3. A compound having the formula:

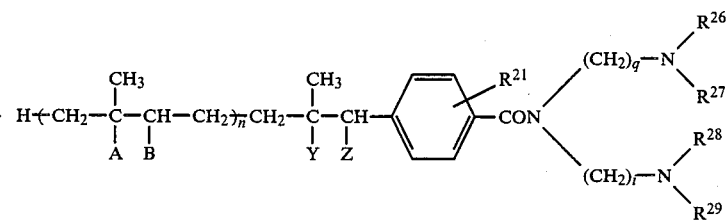

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; q and i are each an integer of 1 to 5; $R^{21}$ is hydrogen, a lower alkyl or a halogen atom and $R^{26}$, $R^{27}$, $R^{28}$ and $R^{29}$ are each a lower alkyl, or a pharmaceutically acceptable salt thereof.

4. A compound having the formula:

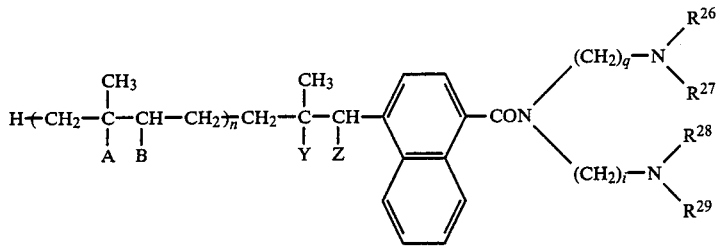

wherein A, B, Y and Z are each a hydrogen, or the pair (1) A and B and/or the pair (2) Y and Z together represent a direct valence bond between the carbon atoms to which they are attached, thereby forming a double bond therebetween; n is an integer of 1 to 3; q and i are each an integer of 1 to 5; and $R^{26}$, $R^{27}$, $R^{28}$ and $R^{29}$ are each a lower alkyl, or a pharmaceutically acceptable salt thereof.

5. A compound having the formula:

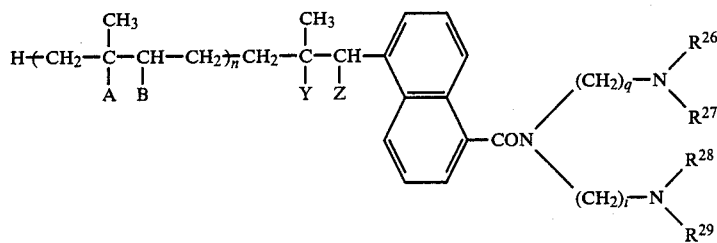

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; q and i are each an integer of 1 to 5; and $R^{26}$, $R^{27}$, $R^{28}$ and $R^{29}$ are each a lower alkyl, or a pharmaceutically acceptable salt thereof.

6. A compound having the formula:

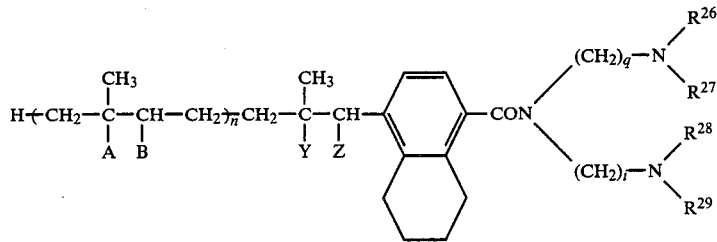

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; q and i are each an integer of 1 to 5; and $R^{26}$, $R^{27}$, $R^{28}$ and $R^{29}$ are each a lower alkyl, or a pharmaceutically acceptable salt thereof.

7. A compound having the formula:

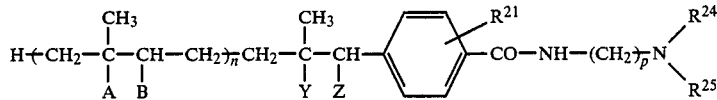

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; p is an integer of from 0–5; $R^{21}$ is hydrogen, a lower alkyl or a halogen atom and $R^{24}$ and $R^{25}$ are each hydrogen or a lower alkyl, or a pharmaceutically acceptable salt thereof.

8. A compound having the formula:

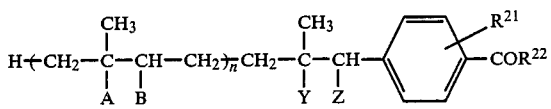

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3 and $R^{22}$ is a group of the formula

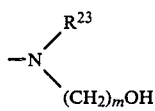

wherein $R^{23}$ is hydrogen or lower alkyl and m is an integer of from 1 to 5,
a group of the formula

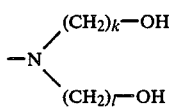

wherein k and l are the same or different and each is an integer of from 1 to 5,
a group of the formula

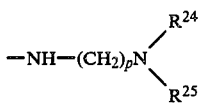

wherein p is an integer of from 0 to 5 and $R^{24}$ and $R^{25}$ are each hydrogen or lower alkyl;
and a group of the formula

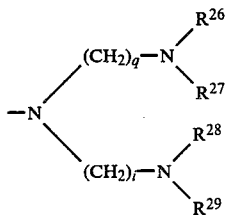

wherein q and i are each an integer of 1 to 5 and $R^{26}$, $R^{27}$, $R^{28}$ and $R^{29}$ are each a lower alkyl, and $R^{21}$ is hydrogen, a lower alkyl or a halogen atom, or a pharmaceutically acceptable salt thereof.

9. A compound having the formula:

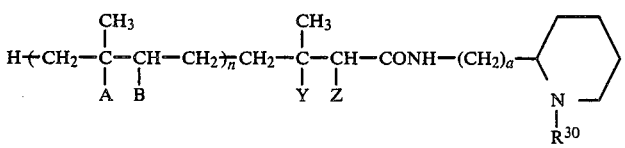

wherein A, B, Y and Z are each hydrogen, or the pair (1) A and B and/or the pair (a) Y and Z together represent a direct valence bond between the carbon atoms to which they are attached, thereby forming a double bond therebetween; n is an integer of 1 to 3; a is 0 or an integer of 1-5 and $R^{30}$ is a lower alkyl group, or a pharmaceutically acceptable salt thereof.

10. A compound having the formula:

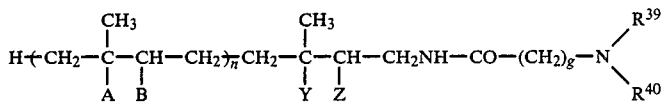

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; where g is an integer of 1 to 5 and $R^{39}$ and $R^{40}$ are each hydrogen or a lower alkyl, or a pharmaceutically acceptable salt thereof.

11. A compound having the formula:

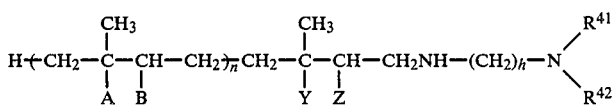

wherein A, B, Y and Z are each hydrogen, or the pair (1) A and B and/or the pair (2) Y and Z together represent a direct valence bond between the carbon atoms to which they are attached, thereby forming a double bond therebetween; n is an integer of 1 to 3; h is an integer of 1 to 5 and $R^{41}$ and $R^{42}$ are each hydrogen or a lower alkyl, or a pharmaceutically acceptable salt thereof.

12. The compound according to claim 1 in which each of the pair A, B and the pair X, Y together represent a direct valence bond between the carbon atoms to which they are attached, thereby forming a double bond therebetween.

13. The compound according to claim 12 in which n is 3.

14. The compound according to claim 2 in which each of the pair A, B and the pair X, Y together represent a direct valence bond between the carbon atoms to which they are attached, thereby forming a double bond therebetween.

15. The compound according to claim 14 in which n is 3.

16. The compound according to claim 3 in which each of the pair A, B and the pair X, Y together represent a direct valence bond between the carbon atoms to which they are attached, thereby forming a double bond therebetween.

17. The compound according to claim 16 in which n is 3.

18. The compound according to claim 4 in which each of the pair A, B and the pair X, Y together represent a direct valence bond between the carbon atoms to which they are attached, thereby forming a double bond therebetween.

19. The compound according to claim 18 in which n is 3.

20. The compound according to claim 5 in which each of the pair A, B and the pair X, Y together represent a direct valence bond between the carbon atoms to which they are attached, thereby forming a double bond therebetween.

21. The compound according to claim 20 in which n is 3.

22. The compound according to claim 6 in which each of the pair A, B and the pair X, Y together represent a direct valence bond between the carbon atoms to which they are attached, thereby forming a double bond therebetween.

23. The compound according to claim 22 in which n is 3.

24. The compound according to claim 7 in which each of the pair A, B and the pair X, Y together represent a direct valence bond between the carbon atoms to which they are attached, thereby forming a double bond therebetween.

25. The compound according to claim 24 in which n is 3.

26. The compound according to claim 8 in which each of the pair A, B and the pair X, Y together represent a direct valence bond between the carbon atoms to which they are attached, thereby forming a double bond therebetween.

27. The compound according to claim 26 in which n is 3.

28. The compound according to claim 9 in which each of the pair A, B and the pair X, Y together represent a direct valence bond between the carbon atoms to which they are attached, thereby forming a double bond therebetween.

29. The compound according to claim 28 in which n is 3.

30. The compound according to claim 10 in which each of the pair A, B and the pair X, Y together represent a direct valence bond between the carbon atoms to which they are attached, thereby forming a double bond therebetween.

31. The compound according to claim 30 in which n is 3.

32. The compound according to claim 11 in which each of the pair A, B and the pair X, Y together represent a direct valence bond between the carbon atoms to which they are attached, thereby forming a double bond therebetween.

33. The compound according to claim 32 in which n is 3.

34. A pharmaceutical composition having antithrombic activity which comprises a therapeutically effective amount of a compound as defined in claim 1, in association with a pharmaceutically acceptable carrier, diluent or vehicle.

35. A pharmaceutical composition having anti-PAF activity which comprises a therapeutically effective amount of a compound as claimed in claim 1, in association with a pharmaceutically acceptable carrier, diluent or vehicle.

* * * * *